(12) United States Patent
Foody et al.

(10) Patent No.: US 10,421,667 B2
(45) Date of Patent: Sep. 24, 2019

(54) PROCESS FOR TREATING LIGNOCELLULOSIC FEEDSTOCK COMPRISING WET OXIDATION

(71) Applicant: Iogen Corporation, Ottawa (CA)

(72) Inventors: Patrick J. Foody, Ottawa (CA); Brian Foody, Ottawa (CA); John Dechman, Ottawa (CA)

(73) Assignee: Iogen Corporation, Ottawa (CA)

(*) Notice: Subject to any disclaimer, the term of this patent is extended or adjusted under 35 U.S.C. 154(b) by 15 days.

(21) Appl. No.: 15/550,584

(22) PCT Filed: Mar. 16, 2016

(86) PCT No.: PCT/CA2016/050290
§ 371 (c)(1),
(2) Date: Aug. 11, 2017

(87) PCT Pub. No.: WO2016/145529
PCT Pub. Date: Sep. 22, 2016

(65) Prior Publication Data
US 2018/0029896 A1 Feb. 1, 2018

Related U.S. Application Data

(60) Provisional application No. 62/232,151, filed on Sep. 24, 2015, provisional application No. 62/133,609, filed on Mar. 16, 2015.

(51) Int. Cl.
| | | |
|---|---|---|
| *C01C 1/24* | (2006.01) | |
| *C05C 3/00* | (2006.01) | |
| *C05D 1/02* | (2006.01) | |
| *C08H 8/00* | (2010.01) | |
| *C12P 19/02* | (2006.01) | |
| *C12P 19/14* | (2006.01) | |
| *C10L 1/02* | (2006.01) | |
| *C12P 7/10* | (2006.01) | |
| *C05F 17/00* | (2006.01) | |
| *C01D 5/00* | (2006.01) | |
| *C01D 5/04* | (2006.01) | |
| *C07G 1/00* | (2011.01) | |
| *C12P 7/16* | (2006.01) | |
| *C12F 3/00* | (2006.01) | |
| *C01C 1/16* | (2006.01) | |

(52) U.S. Cl.
CPC .............. *C01C 1/24* (2013.01); *C01D 5/00* (2013.01); *C01D 5/04* (2013.01); *C05C 3/00* (2013.01); *C05D 1/02* (2013.01); *C05F 17/0045* (2013.01); *C07G 1/00* (2013.01); *C08H 8/00* (2013.01); *C10L 1/02* (2013.01); *C12F 3/00* (2013.01); *C12P 7/10* (2013.01); *C12P 7/16* (2013.01); *C12P 19/02* (2013.01); *C12P 19/14* (2013.01); *C01C 1/164* (2013.01); *C12P 2201/00* (2013.01); *C12P 2203/00* (2013.01); *Y02E 50/10* (2013.01); *Y02E 50/16* (2013.01); *Y02E 50/343* (2013.01); *Y02P 20/145* (2015.11); *Y02W 30/43* (2015.05); *Y02W 30/47* (2015.05)

(58) Field of Classification Search
None
See application file for complete search history.

(56) References Cited

U.S. PATENT DOCUMENTS

| | | | |
|---|---|---|---|
| 2,418,167 | A | 4/1947 | Du Bois |
| 3,562,319 | A | 2/1971 | Brink |
| 4,384,897 | A | 5/1983 | Brink |
| 5,221,357 | A | 6/1993 | Brink |
| 5,789,210 | A | 8/1998 | Ho et al. |
| 5,866,382 | A | 2/1999 | Hallborn et al. |
| 6,423,236 | B1 | 7/2002 | Shiota et al. |
| 6,475,768 | B1 | 11/2002 | Otero et al. |
| 6,582,944 | B1 | 6/2003 | Hallborn et al. |
| 7,527,927 | B1 | 5/2009 | Ho et al. |
| 7,527,951 | B2 | 5/2009 | Londesborough et al. |
| 7,585,652 | B2 | 9/2009 | Foody et al. |
| 7,622,284 | B2 | 11/2009 | Op Den Camp et al. |

(Continued)

FOREIGN PATENT DOCUMENTS

| | | |
|---|---|---|
| GB | 2033366 A | 5/1990 |
| WO | 2006/032282 A1 | 3/2006 |

(Continued)

OTHER PUBLICATIONS

Bensah, E. and Mensah, M., "Chemical Pretreatment Methods for the Production of Cellulosic Ethanol: Technologies and Innovations," International Journal of Chemical Engineering, 2013, pp. 1-21, vol. 2013.
Bhalla, A. et al., "Improved lignocellulose conversion to biofuels with thermophilic bacteria and thermostable enzymes," Bioresource Technology, 2013, pp. 751-759, vol. 128.
Boussaid, A., et al., "Fermentability of the Hemicellulose-Derived Sugars from Steam-Exploded Softwood (Douglas Fir)," , Biotechnology and Bioengineering, 1999, pp. 284-289, vol. 64, No. 3.
Brownell, H. and Saddler, J., "Steam Pretreatment of Lignocellulosic Material for Enhanced Enzymatic Hydrolysis," Biotechnology and Bioengineering, 1987, pp. 228-235, vol. 29.

(Continued)

*Primary Examiner* — Thane Underdahl
(74) *Attorney, Agent, or Firm* — Knobbe, Martens, Olson & Bear, LLP

(57) ABSTRACT

A process for producing one or more products from a lignocellulosic feedstock comprising treating the lignocellulosic feedstock to produce sugar in one or more stages comprising addition of acid, base or a combination thereof and introduction of heat. The addition of the acid, base, or a combination thereof produces a salt. The sugar is fermented to produce a fermentation product and the fermentation product is recovered. A stream comprising the salt is treated by wet oxidation with the introduction of heat. A stream comprising salt resulting from the wet oxidation is provided for use as a salt product or a process chemical for introduction within the process. Heat from the wet oxidation may be supplied to any stage of the process in which heat is introduced.

24 Claims, 5 Drawing Sheets

(56) References Cited

U.S. PATENT DOCUMENTS

| | | | |
|---|---|---|---|
| 8,038,842 B2 | 10/2011 | Retsina et al. |
| 8,247,203 B2 | 8/2012 | Foody et al. |
| 8,268,125 B2 | 9/2012 | Retsina et al. |
| 8,409,836 B2 | 4/2013 | Vehmaanpera et al. |
| 8,506,716 B2 | 8/2013 | Ahring et al. |
| 8,709,770 B2 | 4/2014 | Harlick et al. |
| 8,728,243 B2 | 4/2014 | van der Meulen et al. |
| 8,815,499 B2 | 8/2014 | Alriksson et al. |
| 8,834,633 B2 | 9/2014 | van der Meulen et al. |
| 8,871,475 B2 | 10/2014 | Alriksson et al. |
| 8,911,979 B2 | 12/2014 | Foody et al. |
| 9,012,188 B2 | 4/2015 | Van Heiningen et al. |
| 9,090,915 B2 | 7/2015 | Wang et al. |
| 9,102,951 B2 | 8/2015 | Griffin et al. |
| 9,290,821 B2 | 3/2016 | Blackbourn et al. |
| 9,574,212 B2 | 2/2017 | Foody et al. |
| 2007/0254348 A1 | 11/2007 | Retsina et al. |
| 2009/0118477 A1 | 5/2009 | Hallberg et al. |
| 2010/0056774 A1 | 3/2010 | Anand et al. |
| 2010/0279361 A1 | 11/2010 | South et al. |
| 2011/0039318 A1 | 2/2011 | Lehr |
| 2011/0300586 A1 | 12/2011 | Liu et al. |
| 2012/0041186 A1 | 2/2012 | Pschorn et al. |
| 2012/0073199 A1 | 3/2012 | Lewis |
| 2013/0071903 A1 | 3/2013 | Rowland et al. |
| 2014/0053827 A1 | 2/2014 | Baudel et al. |
| 2014/0054506 A1 | 2/2014 | Melin et al. |
| 2014/0154746 A1 | 6/2014 | Jonsson et al. |
| 2014/0163210 A1 | 6/2014 | Retsina et al. |
| 2014/0178944 A1 | 6/2014 | Parekh et al. |
| 2014/0182582 A1 | 7/2014 | Retsina et al. |
| 2014/0186899 A1 | 7/2014 | Retsina et al. |
| 2014/0186903 A1 | 7/2014 | Retsina et al. |
| 2014/0199740 A1 | 7/2014 | Merrill et al. |
| 2015/0050707 A1 | 2/2015 | Gapes et al. |
| 2015/0259709 A1 | 9/2015 | Retsina et al. |

FOREIGN PATENT DOCUMENTS

| | | |
|---|---|---|
| WO | 2006/034590 A1 | 4/2006 |
| WO | 2006/034591 A1 | 4/2006 |
| WO | 2006/128304 A1 | 12/2006 |
| WO | 2008/041840 A1 | 4/2008 |
| WO | 2010/022511 A1 | 3/2010 |
| WO | 2011/080131 A2 | 7/2011 |
| WO | 2012/117161 A1 | 9/2012 |
| WO | 2013/113579 A1 | 8/2013 |
| WO | 2014/106222 A2 | 7/2014 |
| WO | 2014/113615 A1 | 7/2014 |
| WO | 2016/145527 A1 | 9/2016 |
| WO | 2016/145528 A1 | 9/2016 |
| WO | 2016/145530 A1 | 9/2016 |
| WO | 2016/145531 A1 | 9/2016 |

OTHER PUBLICATIONS

Bura, et al., "Moving towards commercialization of lignocellulosic biomass to fuels to chemicals. How to deal with heterogeneous biomass?" University of Washington Biofuels and Bioproducts Laboratory, 2012.
Bura, R., et al., "Influence of Xylan on the Enzymatic Hydrolysis of Steam-Pretreated Corn Stover and Hybrid Poplar," Biotechnol Prog, 2009, pp. 315-322, vol. 25, No. 2.
Bura, R., et al., "SO2-Catalyzed Steam Explosion of Corn Fiber for Ethanol Production", Applied Biochemistry and Biotechnology, 2002, pp. 59-72, vols. 98-100.
Carrasco, C., et al., "SO2-catalysed steam pretreatment of quinoa stalks," J Chem Technol Biotechnol, 2015, pp. 64-71, vol. 90.
Carrasco, C., et al., "SO2-catalyzed steam pretreatment and fermentation of enzymatically hydrolyzed sugarcane bagasse," Enzyme and Microbial Technology, 2010, pp. 64-73, vol. 46.
Carrasco, C., "Arabinosylated phenolics obtained from SO2-steam-pretreated sugarcane bagasse," Journal of Chemical Technology and Biotechnology, 2012, pp. 1723-1726, vol. 87.
Chacha, N., et al., "Steam Pretreatment of Pine (*Pinus patula*) Wood Residue for the Production of Reducing Sugars," Cellulose Chemistry and Technology, 2011, pp. 495-501, vol. 45 (7-8).
Chandra, R., et al., "Enhancing Hemicellulose Recovery and the Enzymatic Hydrolysis of Cellulose by Adding Lignosulfonates during the Two-Stage Steam Pretreatment of Poplar," ACS Sustainable Chem Eng, 2015, pp. 986-991, vol. 3.
Cheng et al., "High titer and yield ethanol production from undetoxified whole slurry of Douglas-fir forest residue using pH profiling in SPORL," Biotechnology for Biofuels, 2015, pp. 1-10, vol. 8:22.
Clark, T.A, et al., "Steam Explosion of the Softwood Pinus Radiata with Sulphur Dioxide Addition. II. Process Characterisation," Journal of Wood Chemistry and Technology, 1989, pp. 135-166, vol. 9:2.
Clark, T.A. et al., "Steam Explosion of the Softwood Pinus Radiata with Sulphur Dioxide Addition. I. Process Optimization," Journal of Wood Chemistry and Technology, 1987, pp. 373-403, vol. 7:3.
Corrales et al., "Structural evaluation of sugar cane bagasse steam pretreated in the presence of CO2 and SO2," Biotechnology for Biofuels, 2012, pp. 1-8, vol. 5:36.
De Bari et al., "SO2-Catalyzed Steam Fractionation of Aspen Chips for Bioethanol Production: Optimization of the Catalyst Impregnation," Ind. Eng. Chem. Res, 2007, pp. 7711-7720, vol. 46.
Dekker, R.F.H. et al,. "Enzymic Saccharification of Sugarcane Bagasse Pretreated by Autohydrolysis-Steam Explosion," Biotechnology and Bioengineering, 1983, pp. 3027-3048, vol. XXV.
Dekker, Robert F. H., "The Utilization of Autohydrolysis-Exploded Hardwood (*Eucalyptus regnans*) and Softwood (*Pinus radiata*) Sawdust for the Production of Cellulolytic Enzymes and Fermentable Substrates," Biocatalysis, 1987, pp. 63-75, vol. 1.
Ehsanipour, Mandana "Bioconversion of lignocellulosic hydrolysate to acetic acid using Moorella thermoacetica," a thesis submitted in partial fulfillment of the requirements for the degree of Master of Science at University of Washington, 2015.
Eklund et al., "The Influence of SO2 and H2SO4 Impregnation of Willow Prior to Steam Pretreatment," 1995, Bioresource Engineering, pp. 225-229, vol. 52.
Elander, et al., "Summary of findings from the Biomass Refining Consortium for Applied Fundamentals and Innovation (CAFI): corn stover pretreatment," 2009, Cellulose, pp. 649-659, vol. 16.
Ewanick et al., "The effect of biomass moisture content on bioethanol yields from steam pretreated switchgrass and sugarcane bagasse," 2011, Bioresource Technology, pp. 2651-2658, vol. 102.
Galbe et al., "A review of the production of ethanol from softwood," 2002, Appl Microbial Biotechnol, pp. 618-628, vol. 59.
Garlock et al., "Comparative material balances around pretreatment technologies for the conversion of switchgrass to soluble sugars," 2011, Bioresource Technology, pp. 11063-11071, vol. 102.
Gregg et al., "A Techno-Economic Assessment of the Pretreatment and Fractionism Steps of a Biomass-to-Ethanol Process," 1996, Applied Biochemistry and Biotechnology, pp. 711-727, vol. 57/58.
Gu et al., "Fermentative High-Titer Ethanol Production from Douglas-Fir Forest Residue Without Detoxification Using SPORL: High SO2 Loading at Low Temperature," 2016, Industrial Biotechnology, pp. 168-175, vol. 12, No. 3.
Hodge et al., "Soluble and insoluble solids contributions to high-solids enzymatic hydrolysis of lignocellulose," 2008, Bioresource Technology, pp. 8940-8948, vol. 99.
Kumar et al., "Access of Cellulase to Cellulose and Lignin for Poplar Solids Produced by Leading Pretreatment Technologies," 2009, Biotechnol. Prog., pp. 807-819, vol. 25, No. 3.
Lan et al., "High titer ethanol production from SPORL-pretreated lodgepole pine by simultaneous enzymatic saccharification and combined fermentation," 2013, Bioresource Technology, pp. 291-297, vol. 127.
Leu et al., "Substrate-Related Factors Affecting Enzymatic Saccharification of Lignocelluloses; Our Recent Understanding," 2013, Bioenerg. Res., pp. 405-415, vol. 6.
Liu et al., "Effect of Sulfite Pretreatment to Overcome the Recalcitrance of Lignin (SPORL) on Enzymatic Saccharification of Corn Stalk," 2011, Bioresouces, 5001-5011, vol. 6(4).

(56) References Cited

OTHER PUBLICATIONS

Mackie et al., "Effect of Sulphur Dioxide and Sulphuric Acid on Steam Explosion of Aspenwood," 1985, Journal of Wood Chemistry and Technology, pp. 405-425, vol. 5(3).
Mamers et al., "Explosion pretreatment of Pinus radiata woodchips for the production of fermentation substrates," 1984, Apita, pp. 644-649, vol. 37.
Martin et al., "Comparison of the Fermentability of Enzymatic Hydrolyzates of Sugarcane Bagasse Pretreated by Steam Explosion Using Different Impregnating Agents," 2002, Applied Biochemistry and Biotechnology, pp. 699-716, vol. 98-100.
Monavari et al., "Improved One-Step Steam Pretreatment if $SO_2$-Impregnated Softwood with Time-Dependant Temperature Profile for Ethanol Production," 2010, Biotechnol. Prog., pp. 1054-1060, vol. 26, No. 4.
Nguyen et al., "Dilute Acid Pretreatment of Softwoods," 1998, Applied Biochemistry and Biotechnology, pp. 77-89, vol. 70-72.
Shevchenko et al., "Optimization of monosaccharide recovery by post-hydrolysis of the water-soluble hemicellulose component after steam explosion of softwood chips," 2000, Bioresource Technology, pp. 207-211, vol. 72.
Shevchenko et al., "The Nature of Lignin from Steam Explosion/Enzymatic Hydrolysis of Softwood," 1999, Applied Biochemistry and Biotechnology, pp. 867-876, vol. 77-79.
Shi et al., "Sugar yields from dilute sulfuric acid and sulfur dioxide pretreatments and subsequent enzymatic hydrolysis of switchgrass," 2011, Bioresource Technology, pp. 8930-8938, vol. 102.
Shuai et al., "Comparitive study of SPORL and dilute-acid pretreatments of spruce for cellulosic ethanol production," 2010, Bioresource Technology, pp. 3106-3114, vol. 2010.
Sipos et al., "Steam pretreatment of dry and ensiled industrial hemp for ethanol production," 2010, Biomass and Bioenergy, pp. 1-11.
Soderstrom et al. "Effect of Washing on Yield in One- and Two-Step Steam Pretreatment of Softwood for Production of Ethanol," 2004, Biotehncol. Prog., pp. 744-749, vol. 20.
Soderstrom et al., "Separate versus Simultaneous Saccharification and Fermentation of Two-Step Steam Pretreated Softwood for Ethanol Production," 2005, Journal of Wood Chemistry, pp. 187-202, vol. 25.
Soderstrom et al. "Two-Step Steam Pretreatment of Softwood with $SO_2$ Impregnation for Ethanol Production," 2002, Applied Biochemistry and Biotechnology, pp. 5-21, vol. 98-100.
Szengyel et al., "Cellulase Production of Trichoderma reesei Rut C 30 Using Steam-Penetrated Spruce," 2000, Applied Biochemistry and Biotechnology, pp. 679-691, vol. 84-86.
Tengborg et al., "Comparison of $SO_2$ and $H_2SO_4$ Impregnation of Softwood Prior to Steam Pretreatment on Ethanol Production," 1998, Applied Biochemistry and Biotechnology, pp. 3-15, vol. 70-72.
Tengborg et al., "Reduced inhibition of enzymatic hydrolysis of steam-pretreated softwood," 2001, Enzyme and Microbial Technology, pp. 835-844, vol. 28.
Tian et al., "Comparisons of SPORL and Dilute Acid Pretreatments for Sugar and Ethanol Productions from Aspen," 2011, Biotechnol. Prog. pp. 419-427, vol. 27, No. 2.
Tian et al., "Robust cellulosic ethanol production from SPORL-pretreated lodgepole pine using an adapted strain *Saccharomyces cerevisiae* without detoxification," 2010, Bioresource Technology, pp. 8678-8685, vol. 101.
Trajano et al. "Fundamentals of Biomass Pretreatment at Low pH," 2013, Aqueous Pretreatment of Plant Biomass for Biological and Chemical Conversion to Fuels and Chemicals, pp. 103-128.
Vera et al., "Synergetic effects of mixing hybrid poplar and wheat straw biomass for bioconversion processes," 2015, Biotechnol Biofuels, pp. 1-10, vol. 8:226.
Von Sivers et al., "A Techno-Economical Comparison of Three Processes for the Production of Ethanol from Pine," 1995, Bioresource Technology, pp. 43-52, vol. 51.
Wang et al., "Lignosulfonate and elevated pH can enhance enzymatic saccharification of lignocelluloses," 2013, Biotechnology for Biofuels, pp. 1-10, vol. 6:9.
Wang et al., "Ethanol production from poplar wood through enzymatic saccharification and fermentation by dilute acid and SPORL pretreatments," 2012, Fuel, pp. 606-614, vol. 95.
Wang et al., "Sulfite Pretreatment to Overcome Recalcitrance of Lignocellulose (SPORL) for Robust Enzymatic Saccharification of Hardwoods," 2009, Biotechnol. Prog., pp. 1086-1093, vol. 25, No. 4.
Wayman et al., "Hydrolysis of Biomass by Sulphur Dioxide," 1984, Biomass, pp. 183-191, vol. 6.
Wayman et al., "SO2 Catalysed Prehydrolysis of Coniferous Wood for Ethanol Production," 1986, Biotechnology Letters, pp. 749-752, vol. 8, No. 10.
Wiman et al., "Cellulose accessibility determines the rate of enzymatic hydrolysis of steam-pretreated spruce," 2012, Bioresource Technology, pp. 208-215, vol. 126.
Wolfinger et al., "Modeling of the Acid Sulfite Pulping Process.—Problem Definition and Theoretical Approach for a solution with the Main Focus on the Recovery of Cooking Chemicals," 2004, Lenzinger Berichte, pp. 35-45, vol. 83.
Wooley, Bob, "Production of 1,000 Gallons of BioJet," 2015, Presentation from 2015 Annual Meeting of Northwest Advanced Renewables Alliance (NARA).
Wyman et al., "Comparative data on effects of leading pretreatments and enzyme loadings and formulations on sugar yields from different switchgrass sources," 2011, Bioresource Technology, 11052-11062, vol. 102.
Wyman et al., "Comparitive Sugar Recovery and Fermentation Data Following Pretreatment of Poplar Wood by Leading Technologies," 2009, Biotechnol. Prog., pp. 333-339, vol. 25, No. 2.
Fan et al., "Optimization of SO2-catalyzed hydrolysis of corncob for xylose and xylitol production," 2014, J Chem Technol Biotechnol, pp. 1720-1726, vol. 89.
Zhang et al., "Sulfite (SPORL) pretreatment of switchgrass for enzymatic saccharification," 2013, Bioresource Technology, pp. 127-134, vol. 129.
Zhou et al., "Bioconversion of Beetle-Killed Lodgepole Pine Using SPORL: Process Scale-Up Design, Lignin Coproduct, and High Solids Fermentation without Detoxification," 2013, Industrial & Engineering Chemistry Research, pp. A-I.
Zhu et al., "Woody biomass pretreatment for cellulosic ethanol production: Technology and energy consumption evaluation," 2010, Bioresource Technology, pp. 4992-5002, vol. 101.
Zhu et al., "Using sulfite chemistry for robust bioconversion of Douglas-fir forest residue to bioethanol at high titer and lignosulfonate: A pilot-scale evaluation," 2015, Bioresource Technology, pp. 390-397, vol. 179.
Zhu et al., "Ethanol production from SPORL-pretreated lodgepole pine: preliminary evaluation of mass balance and process energy efficiency," 2010, App Microbiol Biotechnol, pp. 1355-1365, vol. 86.
Zhu et al., "High Titer Ethanol Production from Forest Residue Using Sulfite Mill Pulping Chemistry," 2015, Presentation at 2015 TAPPI IBBC.
Zhu et al., "High titer ethanol production from simultaneous enzymatic saccharification and fermentation of aspen at high solids: A comparison between SPORL and dilute acid pretreatments," 2011, Bioresource Technology, pp. 8921-8929, vol. 102.
Zhu et al., "On Polydispersity of Plant Biomass Recalcitrance and its Effects on Pretreatment Optimization for Sugar Production," 2011, Bioenerg. Res., pp. 201-210, vol. 4.
Zhu et al., Quantitative predictions of bioconversion of aspen by dilute acid and SPORL pretreatments using a unified combined hydrolysis factor (CHF), 2012, Process Biochemistry, pp. 785-791, vol. 47.
Zhu et al., "Sulfite pretreatment (SPORL) for robust enzymatic saccharification of spruce and red pine," 2009, Bioresource Technology, pp. 2411-2418, vol. 100.
Barakat et al., "Effect of lignin-derived and furan compounds found in lignocellulosic hydrolysates on biomethane production", Bioresource Technology, 2012, vol. 104, pp. 90-99.

(56) References Cited

OTHER PUBLICATIONS

Taherzadeh and Karimi, "Pretreatment of Lignocellulosic Wastes to Improve Ethanol and Biogas Production: A review". Int. J. Mol. Sci., 2008, vol. 9, No. 9, pp. 1621-1651.

Monlau et al., "Lianocellulosic Materials into Biohydrogen and Biomethane: Impact of Structural Features and Pretreatment", Critical Reviews in Environmental Science and Technology, 2013, vol. 43, No. 3, pp. 260-322.

Matsakas et al., "Sequential Parametric Optimization of Methane Production from Different Sources of Forest Raw Material", Front. Microbiol., 2015, vol. 6, Article 1163.

Cavka et al., "Ozone Detoxification of Steam-Pretreated Norway Spruce", Biotechnol. Biofuels, 2015, vol. 8, p. 196.

Nguyen et al., "Two-Stage Dilute Acid Pretreatment of Softwoods," 2000, Applied Biochemistry and Biotechnology, 561-576, vol. 84-86.

Ohgren et al., "Optimization of Steam Pretreatment of SO2-Impregnated Corn Stover for Fuel Ethanol Production," 2005, Applied Biochemistry and Biotechnology, pp. 1055-1067, vol. 121-124.

Pedersen et al., "Low temperature lignocellulose pretreatment: effects and interactions of pretreatment pH are critical for maximizing enzymatic monosaccharide yields from wheat straw," 2011, Biotechnology for Biofuels, pp. 1-10, vol. 4:11.

Rakkolainen et al., "SO2-Ethanol-Water Fractionation of Forest Biomass and Implications for Biofuel Production by Abe Fermentation," 2010, Cellulose Chem. Technol., pp. 19-145, vol. 44.

Ramos et al. "Characterization of Residual Lignin after SO2-Catalyzed Steam Explosion and Enzymatic Hydrolysis of Eucalyptus viminalis Wood Chips," 1999, J. Agric. Food Chem., pp. 2295-2302, vol. 47.

Ramos et al., "Comparison of Steam Pretreatment of Eucalyptus, Aspen, and Spruce Wood Chips and their Enzymatic Hydrolysis," 1992, Applied Biochemistry and Biotechnology, pp. 37-48, vol. 34/35.

Ramos et al., "Effect of enzymatic hydrolysis on the morphology and fine structure of pretreated cellulosic residues," 1993, Enzyme Microb. Technol., pp. 821-831, vol. 15.

Sassner et al., "Steam Pretreatment of Salix with and without SO2 Impregnation for Production of Bioethanol," 2005, Applied Biochemistry and Biotechnology, pp. 1101-1117, vol. 121-124.

Schell et al., "A Technical and Economic Analysis of Acid-Catalyzed Steam Explosion and Dilute Sulfuric Acid Pretreatments Using Wheat Straw or Aspen Wood Chips," 1991, Applied Biochemistry and Biotechnology, pp. 87-97, vol. 28/29.

Schell et al., "Pretreatment of Softwood by Acid-Catalyzed Steam Explosion Followed by Alkali Extraction," 1998, Applied Biochemistry and Biotechnology, pp. 17-24, vol. 70-72.

Schwald et al., "Assessment of Pretreatment Conditions to Obtain Fast Complete Hydrolysis on High Substrate Concentrations," 1989, Applied Biochemistry and Biotechnology, pp. 29-44, vol. 21/21.

Sendelius et al., "Steam Pretreatment Optimisation for Sugarcane Bagasse in Bioethanol Production," 2005, Master of Science Thesis, Lund University, Sweden.

International Preliminary Report on Patentability dated Sep. 19, 2017 for PCT Application No. PCT/CA2016/050290, filed Mar. 16, 2016, 6pgs.

Office Action issued in U.S. Appl. No. 15/550,515 dated May 3, 2019.

PROCESS FOR TREATING LIGNOCELLULOSIC FEEDSTOCK COMPRISING WET OXIDATION

CROSS-REFERENCE TO RELATED APPLICATIONS

This application is a national stage application of PCT/CA2016/050290 having an international filing date of Mar. 16, 2016, which claims the priority benefit of provisional application No. 62/133,609, filed Mar. 16, 2015, and provisional application No. 62/232,151, filed Sep. 24, 2015, each of which is incorporated herein by reference.

TECHNICAL FIELD

The present invention relates to a process for treating lignocellulosic feedstock and in particular relates to a process for producing one or more products from a lignocellulosic feedstock comprising a wet oxidation.

BACKGROUND

The production of fuel ethanol, or other fuels and chemicals, from lignocellulosic feedstocks provides an attractive alternative to the feedstocks predominantly used to date such as corn starch, sugar cane, and sugar beets. The production of fermentation products from these latter sources cannot increase much further as most of the farmland suitable for the production of these crops is in use. Cellulose is an abundant natural polymer, so there is an enormous untapped potential for its use as a source for fuels and chemicals. Also, lignocellulosic feedstocks to be used for fuel or chemical production are inexpensive as they have limited use.

The conversion of lignocellulosic feedstocks to a fermentation product is usually carried out with a pretreatment process prior to subsequent steps carried out to liberate glucose from the cellulose contained in the feedstock. Pretreatment makes the feedstock more amenable to subsequent conversion of the cellulose to glucose carried out with cellulase enzymes. The glucose can then be converted to a fermentation product such as ethanol by yeast or bacterium using known methods.

The fermentation product is recovered, meaning that it is concentrated and/or purified from a fermented solution. If ethanol or butanol is the fermentation product, the recovery is carried out by distillation, often with further concentration by molecular sieves or membrane extraction. A product-depleted stream resulting from the recovery of the fermentation product contains components besides the fermentation product, such as unfermented sugars, organic salts, and in some instances lignin. Such product-depleted stream may further comprise a certain level of fermentation product not removed by the recovery.

However, there are numerous challenges associated with producing a fermentation product from lignocellulosic feedstock. In order for commercialization to be more widespread, it is desirable to reduce the costs associated with energy usage, acid and/or base addition, and/or salt processing.

For example, the pretreatment is usually conducted at elevated temperature, often above 160° C. This requires a significant input of energy, which negatively impacts process economics. This energy can be supplied at least in part by the combustion of lignin, which is a byproduct of the cellulose conversion process. Although the use of lignin generated during the process is advantageous in that it can reduce the use of fossil fuels, it nonetheless presents several disadvantages. For instance, separation of lignin, which is typically conducted after hydrolysis of the cellulose with cellulase enzymes, requires an additional unit operation often employing specialized filtration equipment, which adds cost. Moreover, separation of the lignin from a hydrolyzate produced by enzymatic hydrolysis can result in sugar loss, which in turn can impact the yield of the fermentation product such as ethanol. A further drawback is that the separated lignin is usually wet, often containing 50% water, thus requiring significant energy for evaporation.

Another drawback of processes to produce products from lignocellulosic feedstocks is that the chemical used to pretreat the feedstock to prepare it for subsequent enzymatic hydrolysis with cellulase can be expensive. Further, if an acid or base is used in the pretreatment, the pH of the pretreated feedstock generally needs to be adjusted to a pH that is within a range that is compatible with cellulase enzymes and/or fermentation microorganisms. Conventionally, cellulase enzymes perform best at a pH of 4 to 6, although genetically modified enzymes are being developed that perform well over a wider range of pH values. However, the addition of an acid or base to adjust the pH of the pretreated feedstock to a suitable range increases chemical consumption, thereby adding further cost to the process.

Moreover, the addition of acid or base to the pretreated feedstock can lead to the production of organic and inorganic salts. Examples of such salts include acetate, sulfate and/or sulfite salts. Inorganic salts can be especially problematic to handle, particularly in downstream processes as described below. These inorganic salts are often carried through to the product-depleted stream remaining after the recovery of the fermentation product. One method for waste water treatment is anaerobic digestion, which produces methane by microbially breaking down organic components. However, the inorganic salts, particularly sulfur-containing salts, can reduce the efficiency of anaerobic digestion. While removal of inorganic salts prior to anaerobic digestion is possible, this also adds cost.

Although the pretreatment of lignocellulosic feedstock followed by enzymatic hydrolysis is described above, the lignocellulosic feedstock may also be treated with acid or base to hydrolyze both the xylan and cellulose component of the feedstock to produce sugar without a subsequent enzymatic hydrolysis step. Such processes may use harsher conditions than acid or alkali pretreatment processes and are often referred to as dilute or concentrated acid or alkali hydrolysis processes. Notably, many of the same problems arising from the addition of relatively dilute acid and/or base during pretreatment may arise in acid or alkali hydrolysis processes as well (e.g. that are not enzymatic). Furthermore, some processes to produce sugar involve no addition or low concentrations of acid and/or base. Salts arising from the feedstock itself, however, could present problems during such processes.

SUMMARY

In accordance with one embodiment, a process for a treating lignocellulosic feedstock including a wet oxidation is provided. For example, in one embodiment streams comprising lignin, certain pretreatment chemicals, or a combination thereof are subject to the wet oxidation. Advantageously, the wet oxidation may generate energy for the process, may eliminate process steps, and/or may generate a salt stream that is readily recovered and/or reused within the process.

In accordance with one aspect of the invention there is provided a process for producing one or more products from a lignocellulosic feedstock comprising: (i) treating the lignocellulosic feedstock to produce sugar in one or more stages comprising addition of acid, base, or a combination thereof, wherein the addition of acid, base or a combination thereof provides at least one of a sulfite, a sulfite salt, sulfurous acid, and a sulfonic acid; and wherein step (i) optionally comprises addition of cellulase enzymes to produce glucose; (ii) fermenting sugar produced in one or more of the stages of step (i) to produce a fermentation product; (iii) recovering the fermentation product, thereby producing a stream of concentrated fermentation product; (iv) treating a process stream by wet oxidation to produce a treated stream comprising a salt, the process stream originating from the process and comprising: (a) lignin, (b) the at least one of a sulfite, a sulfite salt, sulfurous acid, and a sulfonic acid, or (c) a combination thereof; and (v) providing a stream comprising salt from the treated stream of step (iv) for use as a salt product, as a process chemical for introduction within the process, or a combination thereof.

In accordance with one aspect of the invention there is provided a process for producing one or more products from a lignocellulosic feedstock comprising: (i) treating the lignocellulosic feedstock by contacting same with an acid or base with addition of heat to produce a pretreated feedstock; (ii) adjusting the pH of the pretreated feedstock with an acid or base to produce a pretreated feedstock having a pH at which cellulase enzymes can hydrolyze cellulose to glucose, wherein the addition of acid or base provides at least one of a sulfite, a sulfite salt, sulfurous acid, and a sulfonic acid; (iii) hydrolyzing the pretreated feedstock with cellulase enzymes to produce glucose; (iv) fermenting at least the glucose to produce a fermentation product; (v) recovering the fermentation product, thereby producing a stream of concentrated fermentation product; (vi) treating a process stream, which originates from the process and comprises the at least one of a sulfite, a sulfite salt, sulfurous acid, and a sulfonic acid, by wet oxidation to produce a treated stream comprising a salt; and (vii) providing a stream comprising salt from the treated stream of step (vi) for use as a salt product, as a process chemical for introduction within the process, or a combination thereof.

In accordance with one aspect of the invention there is provided a process for producing one or more products from a lignocellulosic feedstock comprising: (i) treating the lignocellulosic feedstock by contacting same with at least heat to produce a pretreated feedstock, the treatment including adding an acid; (ii) optionally adjusting the pH of the pretreated feedstock with a base to produce a pretreated feedstock having a pH at which cellulase enzymes can hydrolyze cellulose to glucose, wherein the addition of the acid, base, or combination thereof provides at least one of a sulfite, a sulfite salt, sulfurous acid, and a sulfonic acid; (iii) hydrolyzing the pretreated feedstock with cellulase enzymes to produce glucose; (iv) fermenting at least the glucose to produce a fermentation product; (v) recovering the fermentation product, thereby producing a stream of concentrated fermentation product; (vi) treating a process stream, which originates from the process and comprises lignin, the at least one of a sulfite, a sulfite salt, sulfurous acid, and a sulfonic acid, or a combination thereof by wet oxidation, to produce a treated stream comprising a salt; (vii) introducing steam energy from step (vi) to the step of pretreating; and (viii) providing a stream comprising salt from the treated stream of step (vi) for use as a salt product, as a process chemical for introduction within the process, or a combination thereof.

BRIEF DESCRIPTION OF THE DRAWING

Exemplary embodiments will now be described in conjunction with the drawings in which.

DETAILED DESCRIPTION

Feedstock

Figure 1:
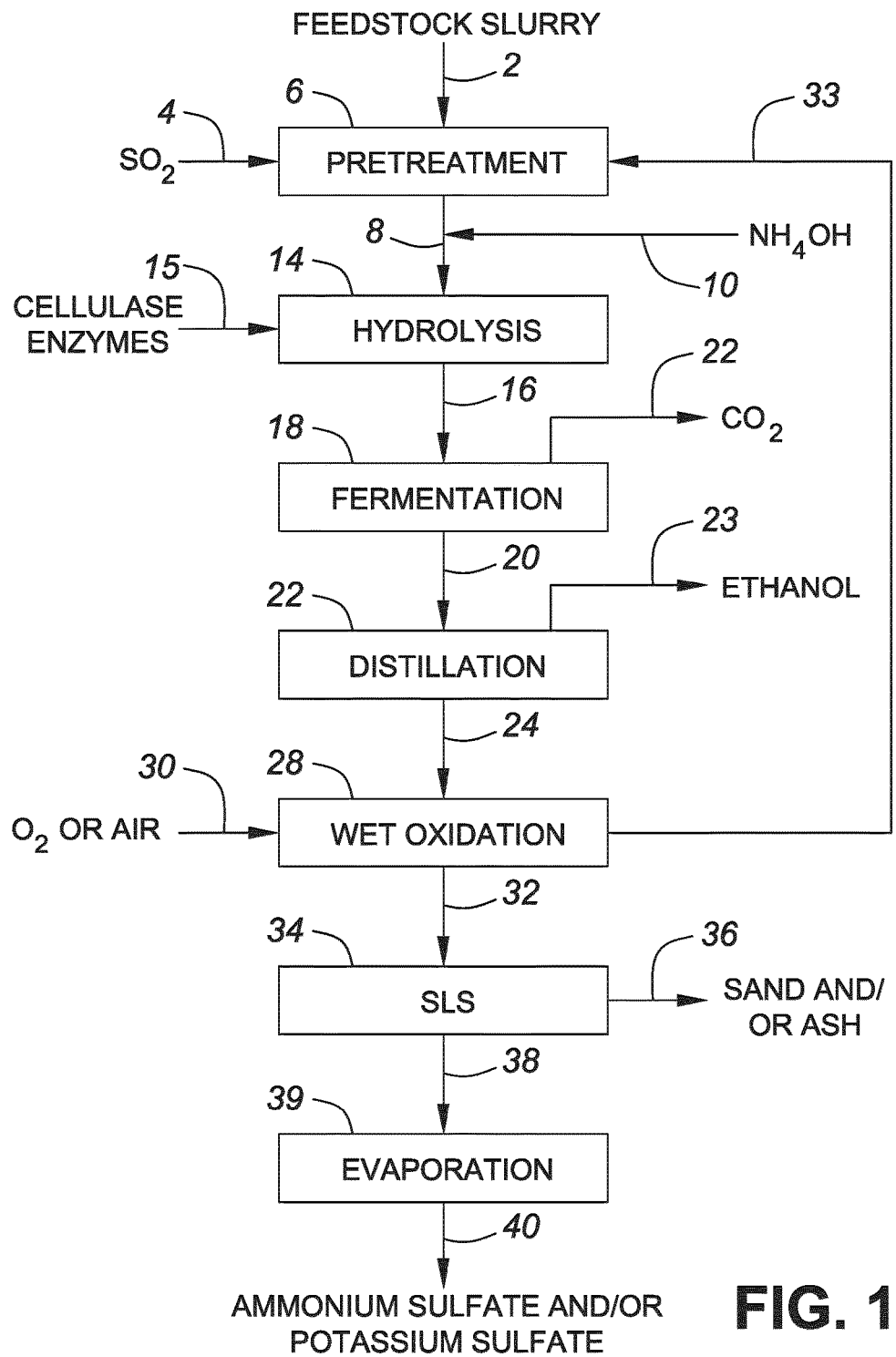
FIG. 1 shows a flow diagram showing a process conducted in accordance with one embodiment of the invention.

Some embodiments of the process of the invention utilize a lignocellulosic feedstock. By the term "lignocellulosic feedstock", it is meant any type of woody or non-woody plant biomass or feedstock derived from plant biomass. The combined content of cellulose, hemicellulose and lignin in the lignocellulosic feedstock is typically greater than 25 wt % (w/w). Sucrose, fructose and starch can be present, but typically in lesser amounts than cellulose and hemicellulose.

Examples of lignocellulosic feedstock are known to those skilled in the art and include: (i) energy crops; (ii) residues, byproducts or waste from the processing of plant biomass in a facility or feedstock derived therefrom; (iii) agricultural residues; (iv) forestry biomass; (v) waste material derived from pulp and paper products; (vi) pulp and paper waste; and/or (vii) municipal waste including components removed from municipal waste.

Energy crops include biomass crops such as grasses, including C4 grasses, such as switch grass, energy cane, sorghum, cord grass, rye grass, *miscanthus*, reed canary grass, C3 grasses such as *Arundo donax* or a combination thereof.

Residues, byproducts or waste from the processing of plant biomass in a facility of feedstock derived therefrom include residues remaining after obtaining sugar from plant biomass such as sugar cane bagasse, sugar cane tops and leaves, beet pulp, or residues remaining after removing sugar from Jerusalem artichoke or residues remaining after grain processing, such as corn fiber, corn stover or bran from grains. Agricultural residues include, but are not limited to soybean stover, corn stover, rice straw, sugar cane tops and/or leaves, rice hulls, barley straw, corn cobs, wheat straw, canola straw, oat straw, oat hulls, corn fiber and corn cobs.

Forestry biomass includes recycled wood pulp fiber, sawdust, hardwood, softwood, trimmings and/or slash from logging operations. Pulp and paper waste includes waste from chemical pulping such as black liquor, spent sulfite liquor, sludge and/or fines.

Municipal waste includes post-consumer material or waste from a variety of sources such as domestic, commercial, institutional and/or industrial sources. For example, the term includes refuse from waste collection and/or sewage sludge.

Lignocellulosic feedstock can be a mixture of fibers that originate from different kinds of plant materials, including mixtures of cellulosic and non-cellulosic feedstocks. In addition, the lignocellulosic feedstock may comprise fresh lignocellulosic feedstock, partially dried lignocellulosic feedstock, full dried lignocellulosic feedstock, or a combination thereof. Moreover, new lignocellulosic feedstock varieties may be produced from any of those listed above by plant breeding or by genetic engineering.

In an embodiment of the invention, the lignocellulosic feedstock is a non-woody lignocellulosic feedstock such as (i) an energy crop, (ii) residues, byproducts or waste from processing of plant biomass or feedstock derived therefrom in a facility, and/or (iii) agricultural residues. In another embodiment of the invention, the lignocellulosic feedstock is straw, stover or an energy crop. As used herein, straw refers to the stem, stalk and/or foliage portion of crops remaining after the removal of starch and/or sugar containing components for consumption. Examples of straw includes, but are not limited to sugar cane tops and/or leaves, oat straw, wheat straw, rye straw, oat straw, rice straw and barley straw. Stover includes the stalk and foliage portion of crops after the removal of starch and/or sugar containing components of plant material for consumption. Examples of stover include but are not limited to soybean stover, sorghum stover and corn stover.

Lignocellulosic feedstocks that have particle sizes of less than about 6 inches may not require size reduction. For feedstocks of larger particle sizes, the feedstock may be subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, hammer mills, tub-grinders, roll presses, refiners and hydrapulpers. In one embodiment, at least 90% by volume of the particles produced from the size reduction may have a length less than between about 1/16 and about 6 inches. Suitable equipment for the particle size reduction is a hammer mill, a refiner or a roll press as disclosed in WO 2006/026863.

Optionally, before, during or subsequent to size reduction, the feedstock can be slurried in liquid, which allows the feedstock to be pumped. The desired weight ratio of water to dry lignocellulosic feedstock solids in the slurry is determined by factors such as pumpability, pipe-line requirements, and other practical considerations. However, it should be understood that the feedstock need not be slurried, but rather could be pretreated without any prior addition of liquid.

Examples of the undissolved solids concentration of the lignocellulosic feedstock are between 20% and 100 wt % or between about 20 wt % and about 80 wt % (w/w).

Treating the Lignocellulosic Feedstock

In one embodiment, the lignocellulosic feedstock is treated in one or more stages to produce sugar(s) for the fermentation. Any of a variety of methods may be used for treating the lignocellulosic feedstock including mechanical, chemical, thermal and/or biological treatments. Fermentable sugar may be obtained from lignocellulosic feedstock using techniques that are known to those of ordinary skill in the art, or later-developed techniques, including, but not limited to those described below.

Two common approaches to produce sugar(s) for fermentation from lignocellulosic feedstock include: 1) a pretreatment (e.g., acid, base, or autohydrolysis) followed by an enzymatic hydrolysis, and 2) a chemical hydrolysis (e.g., with or without a separate pretreatment stage). In each approach, the hemicellulose and/or cellulose in the lignocellulosic feedstock is hydrolyzed into the monomeric sugars that make up the polymer, with the latter being more resistant to hydrolysis.

In general, chemical hydrolysis may be used to hydrolyze both hemicellulose and/or cellulose. For example, when hydrolyzing cellulose, the chemical hydrolysis may use dilute acid under high heat and high pressure, or may use more concentrated acid at lower temperatures and atmospheric pressure. Although chemical hydrolysis of cellulose is included within the scope of the invention, the conditions for chemical hydrolysis of cellulose typically are relatively harsh, thus often producing toxic degradation products that can interfere with fermentation. Accordingly, it is common to provide a pretreatment step (e.g., a relatively mild chemical pretreatment step, wherein a high degree of hydrolysis of the hemicellulose and only a small amount of conversion of cellulose to glucose occurs), followed by an enzymatic hydrolysis that hydrolyzes the cellulose component.

Pretreatment

As discussed above, enzymatic hydrolysis may be preceded by a pretreatment step (e.g., acid, base, or autohydrolysis). The pretreatment step may improve the rate and/or yield of the subsequent enzymatic hydrolysis (e.g., by liberating the cellulose from the lignin and/or by making the cellulose more accessible for the enzyme). Alternatively, or in addition to the addition of acid, base, and/or heat, the pretreatment may include any other pretreatment approaches (e.g., wet oxidation) used in art.

In one embodiment, the lignocellulosic feedstock is pretreated with any suitable acid or base in one or more stages to improve the sugar yield in the subsequent hydrolysis. In general, one or more of these stages may involve heating the lignocellulosic feedstock.

In one embodiment, the lignocellulosic feedstock is pretreated with acid. For example, in one embodiment the lignocellulosic feedstock is treated with a sulfur-containing acid such as sulfurous acid and/or sulfur dioxide.

Some examples of acids that may be used in the pretreatment include gaseous sulfur dioxide ($SO_2$) and/or sulfurous acid ($H_2SO_3$) solutions. As is known in the art, aqueous solutions of $SO_2$, which are commonly referred to as sulfurous acid solutions, may include sulfur dioxide ($SO_2$) and bisulfite ($HSO_3^-$) in solution. When the pH of a stream including sulfurous acid is adjusted (e.g., by adding base), the stream may include any of the following compounds: sulfur dioxide ($SO_2$), bisulfite ($HSO_3^-$), sulfite ($SO_3^{2-}$), sulfite salts, and bisulfite salts. In addition, when the lignocellulosic feedstock is pretreated with sulfur dioxide and/or sulfurous acid, sulfonated species such as sulfonic acids (e.g., lignosulfonates) may be formed. For example, in one embodiment, the addition of acid and/or base provides at least one of a sulfite, a sulfite salt, sulfurous acid, and a sulfonic acid in solution. The phrase "a sulfite", as used herein, may include sulfite and bisulfite. In one embodiment, the addition of the acid and/or base provides a sulfite salt wherein the cation is derived from the feedstock (e.g., such as K2SO3 or KHSO3). The term sulfonic acid(s) encompasses sulfonic acid species, sulfonate species, or both sulfonic acid and sulfonate species. Some examples of sulfonic acids that may be produced by the pretreatment include lignosulfonates (e.g., sulfonated compounds of a relatively high molecular weight) and/or lower molecular weight sulfonic acids.

In one embodiment, the acid pretreatment includes the addition of heat. For example, in one embodiment, the acid pretreatment includes introducing steam and gaseous $SO_2$. Subjecting the lignocellulosic feedstock to an acid pretreatment with gaseous $SO_2$ may advantageously provide a relatively rapid and uniform distribution of acid.

In another embodiment, the acid pretreatment includes soaking the lignocellulosic feedstock in a sulfurous acid solution and heating the soaked feedstock.

Advantageously, adding $SO_2$ and/or sulfurous acid during pretreatment may generate a sulfite or sulfite salt (e.g., directly or indirectly), which are reducing agents and may improve the efficiency of a subsequent enzymatic hydrolysis and/or fermentation. Further advantageously, since the sulfur-containing acid may form a sulfite or sulfite salt in solution, the same may be oxidized to sulfates or sulfate salts, respectively, by the wet oxidation (e.g., as described below). For example, in one embodiment, the acid is a sulfur (IV) containing oxidizable acid.

In one embodiment, addition of acid results in a pH between about 1.0 and about 3.5, wherein the pH is measured at any stage during the time course of the pretreatment and is measured at ambient temperature.

In one embodiment, the acid pretreatment includes the addition of heat. Without being limiting, the addition of heat may result in a maximum temperature between about 160° C. and about 230° C. As will be understood by those having ordinary skill in the art, there may be a time delay in the pretreatment process before the feedstock reaches this temperature range. The above temperatures correspond to those values reached after sufficient application of heat to reach a temperature within this range. In one embodiment, the time that the feedstock is held at the maximum temperature is between about 10 seconds and about 30 minutes. In one embodiment, the feedstock is maintained at the maximum temperature for duration that is between 30 seconds and 5 minutes. Advantageously, maintaining the feedstock at the elevated temperature for less than about 5 minutes, when the acid is $SO_2$, provides an effective pretreatment with reduced costs.

In one embodiment, a base is added after the acid pretreatment to adjust the pH of the feedstock to a pH level compatible with a subsequent enzymatic hydrolysis and/or fermentation. For example, in one embodiment, the pH level is determined in dependence upon the enzymes and/or microbes used in subsequent steps. In general, many suitable enzymes and/or microbes will be active at pH values between 4 and 7, and some may be active outside this range. In one embodiment, sufficient base is added to achieve a pH between 4 and 6. Some examples of suitable bases include ammonia ($NH_3$), ammonium hydroxide ($NH_4OH$), potassium hydroxide (KOH), sodium hydroxide (NaOH), magnesium hydroxide ($Mg(OH)_2$), calcium hydroxide ($Ca(OH)_2$), etc.

In general, the addition of base to the acid-pretreated feedstock may produce one or more salts (e.g., including organic and inorganic salt). For example, in one embodiment the addition of base provides a sulfite salt (e.g., such as $(NH_4)_2SO_3$, $K_2SO_3$, $Na_2SO_3$ $CaSO_3$, $MgSO_3$, $KHSO_3$, etc). In one embodiment, the addition of a base provides a combination of salts (e.g., $K_2SO_3$ and $Na_2SO_3$). Advantageously, using $NH_4OH$ to adjust the pH provides a salt that may be oxidized to $NH_4KSO_4$, which is particularly useful for use a fertilizer and/or land applications.

In general, the alkali may be added to the acid pretreated feedstock after it is cooled, before cooling, or at points both before and after cooling.

In an alternative embodiment, the lignocellulosic feedstock is pretreated with base, also referred to herein as "alkali", to produce an alkali pretreated feedstock. For example, in one embodiment the lignocellulosic feedstock is subjected to an alkali pretreatment with a base. Some examples of suitable bases include $NH_3$, $NH_4OH$, KOH, and NaOH, each of which advantageously is soluble in water. For example, in one embodiment, the lignocellulosic feedstock is treated with a dilute ammonia solution. In some embodiments, the alkali pretreatment may not hydrolyze the hemicellulose in the lignocellulosic feedstock. In some embodiments, the addition of base may alter the crystal structure of the cellulose so that it is more amenable to hydrolysis.

In one embodiment, the alkali pretreatment includes the addition of heat. Without being limiting, alkali pretreatment may be performed at a temperature between about 20° C. and about 200° C. For example, in one embodiment the maximum temperature of the pretreatment is between 100° C. and 200° C. As will be understood by those having ordinary skill in the art, there may be a time delay in the pretreatment process before the feedstock reaches this temperature range. The above temperatures correspond to those values reached after sufficient application of heat to reach a temperature within this range. In one embodiment, the time that the feedstock is held at the maximum temperature is between about 10 seconds and about 120 minutes. In one embodiment, the feedstock is maintained at the maximum temperature for duration that is between 30 seconds and 120 minutes. In one embodiment, the resulting pH is between about pH 9.5 and about pH 12.

In general, when the lignocellulosic feedstock is subject to an alkali pretreatment, an acid may be added after the base addition to adjust the pH of the feedstock to a pH level compatible with a subsequent enzymatic hydrolysis and/or fermentation. In one embodiment, the pH level will be determined in dependence upon the enzymes and/or microbes used in subsequent steps. For example, in one embodiment, wherein the hydrolysis is an enzymatic hydrolysis, the pH is adjusted to a pH compatible with the enzyme. In another embodiment, wherein the hydrolysis is not enzymatic, the pH is adjusted to a level compatible with the fermentation microorganisms. In one embodiment, sufficient acid is added to achieve a pH between 4 and 7. In one embodiment, sufficient acid is added to achieve a pH between 4 and 6. Some examples of acids that may be used to adjust the pH of the alkali pretreated feedstock include gaseous sulfur dioxide ($SO_2$) and sulfurous acid ($H_2SO_3$) solutions. Advantageously, the acid added to adjust the pH may form sulfite ($SO_3^{2-}$) and/or bisulfite ($HSO_3^-$) salts using cation(s) in solution (e.g., from alkali addition and/or from the feedstock itself).

In general, the acid may be added to the pretreated feedstock after it is cooled, before cooling, or at points both before and after cooling.

In one embodiment, the lignocellulosic feedstock is subject to an alkali pretreatment referred to as an Ammonia Freeze Explosion, or Ammonia Fiber Expansion ("AFEX" process). According to this process, the lignocellulosic feedstock is contacted with ammonia or ammonium hydroxide in a pressure vessel. The contact is maintained for a sufficient time to enable the ammonia or ammonium hydroxide to swell (i.e., decrystallize) the cellulose fibers. The pressure is then rapidly reduced which allows the ammonia to flash or boil and explode the cellulose fiber structure. The flashed ammonia may then be recovered according to known processes. However, this only removes a portion of the ammonia and any remaining ammonia may be neutralized with acid to produce an inorganic salt. Alternatively, the ammonia is not recovered by flashing, in which case all or a portion of the ammonia is neutralized with acid.

In yet another embodiment, the lignocellulosic feedstock is subject to an autohydrolysis pretreatment (e.g., a hydrothermal pretreatment involving hot water or steam, where no additional chemicals such as acid or base is added or at concentrations that do not significantly impact the pH). Accordingly, after autohydrolysis an alkali may be added to adjust the pH of the feedstock to a pH level compatible with a subsequent enzymatic hydrolysis and/or fermentation. In general, the pH level will be determined in dependence upon the enzymes and/or microbes used in subsequent steps. In one embodiment, sufficient acid is added to achieve a pH between 4 and 7. Advantageously, since autohydrolysis typically results in a pretreated feedstock that is only slightly acidic, pH adjustment may be accomplished using alkali salts only (e.g., such as $NaHSO_3$ or $Na_2SO_3$ or mixtures thereof). In general, the pH adjustment may occur after the pretreated feedstock is cooled, before cooling, or at points both before and after cooling.

As described above, in some embodiments, the feedstock may be contacted with sulfur dioxide gas and/or a sulfurous acid solution. As would be appreciated by those of skill in the art, the addition of sulfurous acid in the presence of alkali can produce sulfite and bisulfite salts in solution, so the addition of "sulfurous acid" does not necessarily denote that the solution contains this species. The sulfur dioxide may be added to the feedstock in wet form, such as a slurry, a feedstock that is in dry form, or a feedstock that has been subjected to a steam treatment.

In general, the addition of acid, base, and/or heat will be conducted so as to disrupt the fiber structure of the lignocellulosic feedstock and/or to increase its surface area to make it accessible to enzymes (e.g., cellulose enzymes) and/or to increase susceptibility to hydrolysis without enzymes. In general, the pretreatment and/or hydrolysis (e.g., enzymatic or chemical) stages may hydrolyze both the xylan and cellulose component of the feedstock to produce sugar. However, depending on the pretreatment chemical, the pretreatment may be performed such that a certain degree of xylan hydrolysis is achieved and only a small amount of conversion of cellulose to glucose occurs. For example, in some embodiments that do not add acid or base, there may be no or limited hydrolysis of cellulose to produce glucose. In some embodiments that do not include an enzymatic hydrolysis step, the treatment may use harsher conditions (e.g., higher temperatures and/or higher concentrations of acid or base) to provide the hydrolysate.

As discussed above, the feedstock is contacted with the pretreatment acid or base (e.g., as an aqueous solution) before or after heating. For example, in one embodiment, a heated feedstock slurry is contacted with the pretreatment acid or base. In another embodiment, the feedstock is soaked in an aqueous solution comprising the acid or base and subsequently subjected to elevated temperature to pretreat the feedstock. In one embodiment, the treatment includes contacting the feedstock with two or more acids or bases as required.

In one embodiment, the feedstock is contacted with steam prior to or during the pretreatment. For example, in one embodiment the feedstock is treated at elevated temperature without the addition of acid or base.

In one embodiment, the feedstock is heated with steam during or prior to pretreatment. In one embodiment, steam is supplied from wet oxidation, which may be carried out at elevated temperature, as discussed below. Without being limiting, the steam may be introduced to the feedstock during or prior to pretreatment and may be low, medium or high pressure steam. Various devices may be employed to introduce steam to the feedstock, such as commercially available mixing devices designed for introducing steam through spray nozzles.

In one embodiment, the pretreatment, which includes an acid pretreatment, an alkali pretreatment, or an autohydrolysis pretreatment, includes other pretreatment steps (e.g., wet oxidation), which are known in the art.

Chemical Hydrolysis of Cellulose

In one embodiment, the cellulose is hydrolyzed with a chemical, such as acid or base. For example, in one embodiment the cellulose is hydrolyzed to glucose using acid or alkali. In this embodiment, as discussed above, a subsequent step of adding acid or base may be performed to adjust the pH of the solution to be compatible with the fermentation stage of the process.

Enzymatic Hydrolysis of Cellulose

In another embodiment, the cellulose is hydrolyzed to glucose after the pretreatment (e.g., acid or alkali) in a subsequent step that uses cellulase enzymes. Prior to the addition of enzyme, as discussed above, the pH of the feedstock may be adjusted to a value that is suitable for the enzymatic hydrolysis reaction. For example, in one embodiment acid or base is added to provide a pH in the range between about 4 to about 7, or between about 4 and about 6.5, which are optimal pH ranges for many cellulases. The use of alkalophilic cellulases is encompassed within some embodiments of the present invention.

The enzymatic hydrolysis of the cellulose to soluble sugars can be carried out with any type of cellulase enzymes suitable for such purpose and effective at the pH and other conditions utilized, regardless of their source. Among the most widely studied, characterized and commercially produced cellulases are those obtained from fungi of the genera *Aspergillus, Humicola, Chrysosporium, Melanocarpus, Myceliopthora, Sporotrichum* and *Trichoderma*, and from the bacteria of the genera *Bacillus* and *Thermobifida*. Cellulase produced by the filamentous fungi *Trichoderma longibrachiatum* comprises at least two cellobiohydrolase enzymes termed CBHI and CBHII and at least four EG enzymes. As well, EGI, EGII, EGIII, EGV and EGVI cellulases have been isolated from *Humicola insolens* (see Lynd et al., 2002, Microbiology and Molecular Biology Reviews, 66(3):506-577 for a review of cellulase enzyme systems and Coutinho and Henrissat, 1999, "Carbohydrate-active enzymes: an integrated database approach." In Recent Advances in Carbohydrate Bioengineering, Gilbert, Davies, Henrissat and Svensson eds., The Royal Society of Chemistry, Cambridge, pp. 3-12).

In addition to CBH, EG and beta-glucosidase, there are several accessory enzymes that aid in the enzymatic digestion of cellulose (see WO 2009/026722 (Scott), which is incorporated herein by reference and Harris et al., 2010, Biochemistry, 49:3305-3316). These include glycoside hydrolase 61, swollenin, expansin, lucinen and cellulose-induced protein (Cip). Glucose can be enzymatically converted to the dimers gentiobiose, sophorose, laminaribiose and others by beta-glucosidase via transglycosylation reactions.

An appropriate cellulase dosage can be about 1.0 to about 40.0 Filter Paper Units (FPU or IU) per gram of cellulose, or any amount therebetween. The FPU is a standard measurement familiar to those skilled in the art and is defined and measured according to Ghose (Pure and Appl. Chem., 1987, 59:257-268). An example of a cellulase dosage is about 10 to 20 FPU per gram cellulose.

The enzyme dosage may also be measured in units of milligrams of protein per gram of cellulose. An example of a dose in these units is 2 to 20 mg protein per gram cellulose.

The conversion of cellobiose to glucose is carried out by the enzyme β-glucosidase. By the term "β-glucosidase", it is meant any enzyme that hydrolyzes the glucose dimer, cellobiose, to glucose. The activity of the β-glucosidase enzyme is defined by its activity by the Enzyme Commission as EC#3.2.1.21. The β-glucosidase enzyme may come from various sources; however, in all cases, the β-glucosidase enzyme can hydrolyze cellobiose to glucose. The β-glucosidase enzyme may be a Family 1 or Family 3 glycoside hydrolase, although other family members may be used. It is also contemplated that the β-glucosidase enzyme may be modified to include a cellulose binding domain, thereby allowing this enzyme to bind to cellulose.

As discussed above, acid or alkali may be added to the pretreated feedstock to adjust the pH of the feedstock to be compatible with enzyme hydrolysis and/or fermentation. Acid or alkali can be added to the alkali or acid pretreated feedstock, respectively, after it is cooled, before cooling, or at points both before and after cooling. When the process includes an enzymatic hydrolysis, the acid or alkali addition may be part of the pretreatment, may be part of the hydrolysis (e.g., may coincide with the cellulase enzyme addition), or may occur between the pretreatment and enzymatic hydrolysis. For example, the addition point may be upstream or downstream of the location of the enzyme addition. If the enzyme is added upstream of the acid or alkali addition point, the contact time of the enzyme at the lower pH of the pretreated feedstock would typically be minimized to avoid enzyme inactivation. The acid or alkali may be added prior to enzyme addition or simultaneously therewith.

The temperature of the slurry is adjusted so that it is within the optimum range for the activity of the cellulase enzymes. Generally, a temperature of about 45° C. to about 70° C., or about 45° C. to about 65° C., or any temperature therebetween, is suitable for most cellulase enzymes. However, the temperature of the slurry may be higher for thermophilic cellulase enzymes. The duration of the enzymatic hydrolysis may be from 12 to 200 hours or any range therebetween.

The enzymatic hydrolysis and fermentation may be conducted in separate vessels so that each biological reaction can occur at its respective optimal temperature. However, the hydrolysis may be conducted simultaneously with fermentation in a simultaneous saccharification and fermentation (SSF). SSF is typically carried out at temperatures of 35-38° C., which is a compromise between the 50° C. optimum for cellulase and the 28° C. optimum for yeast.

In one embodiment, the hydrolysis provides a stream that includes aqueous sugars and may include soluble lignin and/or lignin solids. For example, in one embodiment, the hydrolysis provides a stream that includes both soluble sugars and insoluble solids such as lignin and/or residual cellulose. In one embodiment, the soluble sugars are separated from the insoluble solids, wherein a stream including the soluble sugars is subject to fermentation, while the stream including the insoluble solids is combusted to provided heat and/or energy either within or external to the process. In this embodiment, the sulfite salts and soluble lignin substantially remain within the aqueous stream comprising the soluble sugars. In another embodiment, the stream including both the soluble sugars and the insoluble solids is subject to fermentation.

Fermentation

Fermentation of sugar resulting from the above treatment may produce one or more of the fermentation products selected from an alcohol, a sugar alcohol, an organic acid and a combination thereof. In general, the fermentation may be conducted in the presence of at least one microorganism that ferments sugars to alcohols. Without being limiting, the fermentation is typically conducted at a pH between about 4.0 and about 6.0, or between about 4.5 and about 6.0.

In one embodiment, the fermentation product is an alcohol, such as ethanol or butanol. For ethanol production, the fermentation is typically carried out with a *Saccharomyces* spp. yeast. Glucose and any other hexoses present in the sugar stream may be fermented to ethanol by wild-type *Saccharomyces cerevisiae*, although genetically modified yeasts may be employed as well, as discussed below. The ethanol may then be distilled to obtain a concentrated ethanol solution. Butanol may be produced from glucose by a microorganism such as *Clostridium acetobutylicum* and then concentrated by distillation.

Xylose and arabinose that are derived from the hemicelluloses may also be fermented to ethanol by a yeast strain that naturally contains, or has been engineered to contain, the ability to ferment these sugars to ethanol. Examples of microbes that have been genetically modified to ferment xylose include recombinant *Saccharomyces* strains into which has been inserted either (a) the xylose reductase (XR) and xylitol dehydrogenase (XDH) genes from *Pichia stipitis* (e.g., U.S. Pat. Nos. 5,789,210, 5,866,382, 6,582,944 and 7,527,927 and European Patent No. 450530) or (b) fungal or bacterial xylose isomerase (XI) gene (e.g., U.S. Pat. Nos. 6,475,768 and 7,622,284). Examples of yeasts that have been genetically modified to ferment L-arabinose include, but are not limited to, recombinant *Saccharomyces* strains into which genes from either fungal (e.g., U.S. Pat. No. 7,527,951) or bacterial (e.g., WO 2008/041840) arabinose metabolic pathways have been inserted.

In practice, the fermentation is typically performed at or near the temperature and pH optimum of the fermentation microorganism. A typical temperature range for the fermentation of glucose to ethanol using *Saccharomyces cerevisiae* is between about 25° C. and about 35° C., although the temperature may be higher if the yeast is naturally or genetically modified to be thermostable. The dose of the fermentation microorganism will depend on other factors, such as the activity of the fermentation microorganism, the desired fermentation time, the volume of the reactor and other parameters. It should be appreciated that these parameters may be adjusted as desired by one of skill in the art to achieve optimal fermentation conditions.

The fermentation may also be supplemented with additional nutrients required for the growth of the fermentation microorganism. For example, yeast extract, specific amino acids, phosphate, nitrogen sources, salts, trace elements and vitamins may be added to the hydrolyzate slurry to support their growth.

The fermentation product is recovered, meaning that it is concentrated and/or purified from a fermented solution/slurry. A remaining stream contains components besides the fermentation product remaining after the recovery, referred to herein as a "product-depleted stream". Non-limiting examples of such components include inorganic salts, unfermented sugars and organic salts. As would be appreciated by those of skill in the art, such stream may comprise a certain amount of product, depending on the extent of recovery achieved.

If ethanol or butanol is the fermentation product, the recovery is often carried out by distillation, typically with further concentration by molecular sieves or membrane extraction. Another example of a recovery method is pervaporation.

The fermentation broth that is sent to distillation is a dilute alcohol solution that may contain solids such as unconverted cellulose and insoluble lignin, and any components added during the fermentation to support growth of the microorganisms.

Microorganisms are potentially present during the distillation depending upon whether or not they are recycled during the fermentation. The broth is preferably degassed to remove carbon dioxide and then pumped through one or more distillation columns to separate the alcohol from the other components in the broth. The mode of operation of the distillation system depends on whether the alcohol has a lower or a higher boiling point than water. Most often, the alcohol has a lower boiling point than water, as is the case when ethanol is distilled.

In those embodiments where ethanol is concentrated, the column(s) in the distillation unit is typically operated in a continuous mode, although it should be understood that batch processes are also within the scope of the present invention. Heat for the distillation process may be introduced at one or more points either by direct steam injection or indirectly via heat exchangers. The distillation unit may contain one or more separate beer and rectifying columns, in which case dilute beer is sent to the beer column where it is partially concentrated. From the beer column, the vapour goes to a rectification column for further purification. Alternatively, a distillation column is employed that comprises an integral enriching or rectification section.

After distillation, the water remaining may be removed from the ethanol rich vapour by a molecular sieve resin, by membrane extraction, or other methods known to those of skill in the art for concentration of ethanol beyond the 95% that is typically achieved by distillation. The ethanol vapour may then be condensed and denatured.

A still bottoms stream remaining after ethanol distillation and containing solids is withdrawn from the bottom of one or more of the column(s) of the distillation unit. This stream may contain inorganic salts, unfermented sugars, organic salts, unconverted cellulose, soluble lignin, and/or lignin solids.

When the alcohol has a higher boiling point than water, such as butanol, the distillation is run to remove the water and other volatile compounds from the alcohol. The water vapor exits the top of the distillation column.

Wet Oxidation

By the term "wet oxidation", it is meant oxidizing a process stream under any suitable conditions in which water is present. For example, in one embodiment the process stream subjected to wet oxidation contains at least 80% by weight water (w/w). In another embodiment, the process stream subjected to wet oxidation contains at least 90% by weight water (w/w).

In one embodiment, the wet oxidation is conducted on any process stream comprising salt. An example of a process stream that can be subjected to wet oxidation is a stream remaining after recovery of the fermentation product, such as, for example, a product-depleted stream. An example of such a product-depleted stream is a still bottoms stream. Advantageously, subjecting the still bottoms stream to wet oxidation may depolymerize lignin therein (e.g., soluble and/or insoluble) and/or provide a sulfate salt. For example, in one embodiment, wet oxidation of the still bottoms converts lignin and/or other organic material to acetic acid and/or $CO_2$. It should be understood that other streams comprising one or more salts may be fed to the wet oxidation as well. In addition, two or more streams can be subjected to wet oxidation. Such streams can be added separately to the wet oxidation or combined previously to form a mixture that is then fed to wet oxidation.

In one embodiment, the stream subjected to wet oxidation includes one or more salts that arise at least in part from the addition of process chemicals. As described above, salts may be produced upon the addition of acid or base to the pretreated feedstock. However, salts present in the stream subjected to wet oxidation may also arise at least in part from the feedstock itself. Without being limiting, lignocellulosic feedstock often has a pH of between 6 and 10 due to the presence of the alkali minerals, such as potassium carbonate. Addition of a sulfur dioxide, sulfurous acid, and/or another chemical that provides sulfites to the feedstock, for example, whether during pretreatment or to neutralize or partially neutralize the feedstock, may produce sulfite salts (e.g., potassium sulfite).

Examples of oxidants are air, oxygen, ozone, hydrogen peroxide, or other known oxidants. In one embodiment of the invention, the oxidant is air or oxygen. Typically, an oxygen stream is purified from air.

The oxidant may be added at a concentration corresponding to 30% to 250% of the chemical oxygen demand (COD) of the product-depleted stream. For example, in one embodiment, the stream fed to wet oxidation has a COD between about 10 g/L and 100 g/L. In general, the pressure of the system may be selected and/or maintained to provide a specific concentration of oxidant and/or to prevent excessive evaporation. In one embodiment, the partial pressure of oxygen is between 0.15 MPa (~22 psi) and 11 MPa (~1600 psi), or between 0.3 MPa (~50 psi) and 1.4 MPa (~200 psi). In one embodiment, wherein an air stream is used, the total pressure is between about 2 MPa (~290 psi) and about 22 MPa (~3200 psi). As would be appreciated by those of skill in the art, lower concentrations of oxidant during the wet oxidation will result in a less complete oxidation than higher concentrations. Thus, the concentration of oxidant added during the wet oxidation step may vary depending on the degree of wet oxidation desired.

In general, the wet oxidation conditions may be selected to achieve a suitable level of oxidation and may depend on the particular oxidant and/or reaction temperature that is utilized. In one embodiment wherein the oxidant is air or oxygen, the treatment temperature is between about 140° C. and about 330° C. In another embodiment wherein the oxidant is air or oxygen, the treatment temperature is between about 140° C. and about 250° C.

In embodiments that conduct the wet oxidation at elevated temperatures, the heat may be provided by any suitable method. In one embodiment, the stream fed to wet oxidation is heated by direct steam injection (e.g., before it enters the reactor and/or while resident within the reactor). For example, in one embodiment, the reactor is filled with water and/or slurry which is then heated by direct steam injection. In another embodiment, the stream fed to wet oxidation is heated indirectly (e.g., using steam and/or electricity). For example, in one embodiment, one or more external heaters are provided to heat the stream before it enters the reactor and/or while resident within the reactor. In yet another embodiment, one or more heat exchangers are provided to heat the stream before it enters the reactor and/or while resident within the reactor. For example, in one embodiment, heat generated during the wet oxidation and/or excess heat used in the wet oxidation is used to preheat the stream fed to the wet oxidation (e.g., via a heat exchanger). With regard to the former, the wet oxidation may be an exothermic reaction that produces heat and/or steam that may be used to preheat the stream fed to wet oxidation. In one embodiment, sufficient heat is generated during the wet oxidation to allow the wet oxidation to be self-sustaining (e.g., require no additional heat within the reactor). In another embodiment, one or more heaters are used to maintain the predetermined temperature within the reaction. In one embodiment, the energy generated during the process may be used to maintain the process temperature and/or may be used for heat integration within the system (e.g., in pretreatment and/or in recovering salts). In one embodiment a catalyst is added to the wet oxidation.

The pH may range from about 2 to about 12. In one embodiment, the pH is adjusted by adding acid or alkali to the process stream or during the wet oxidation step. In one embodiment, the pH is adjusted to a relatively low pH selected to avoid carbonates and/or keep $NH_3$ in solution.

The duration of the wet oxidation with air or oxygen includes any suitable time period. In one embodiment, the reaction time is within a range from 10 minutes to 2 hours. If ozone is used as the oxidant the temperature may range from 0° C. to about 60° C. and the treatment duration may be between about 5 and about 30 minutes. In this embodiment, the reactor may be cooled. It should be appreciated that the foregoing treatment conditions are non-limiting and can be varied as required to obtain a suitable level of wet oxidation. The wet oxidation can be conducted in batch or continuous mode. An example of a known commercially available unit for conducting the wet oxidation step is a Zimpro® wet oxidation unit available from Siemens.

The wet oxidation produces a treated stream, which may be processed further to obtain inorganic salt for use as a fertilizer. Examples of steps for recovering inorganic salt are described below. During wet oxidation, any sulfite compounds that are present may be oxidized to sulfate compounds. For example, in one embodiment the wet oxidation converts sulfite ($SO_3^{2-}$) to sulfate ($SO_4^{2-}$), bisulfate ($HSO_3^-$) to bisulfate ($HSO_4^-$), sulfite salts (e.g., $(NH_4)_2SO_3$) to sulfate salts (e.g., $(NH_4)_2SO_4$), and sulfurous acid $SO_2/H_2SO_3$ to sulfuric acid ($H_2SO_4$).

Advantageously, oxidizing sulfite salts results in the production of sulfate salts such as ammonium sulfate and/or potassium sulfate, which finds use as a fertilizer. For example, in embodiments where the feedstock is pretreated with sulfur dioxide and/or sulfurous acid the pretreated feedstock stream may include the hydrogen sulfite ion $HSO_3^-$, which is a reducing agent, which may form an ammonium sulfite salt if ammonium hydroxide is added, and then may be converted to an ammonium sulfate salt as a result of the wet oxidation. Advantageously, when the pretreatment includes contacting the feedstock with sulfur dioxide and/or sulfurous acid (e.g., a sulfur-containing oxidizable acid) to prepare the feedstock for a subsequent enzymatic hydrolysis, the wet oxidation may remove some of the solids/organic material and may oxidize the sulfites and/or sulfur-containing compounds derived therefrom (e.g., such that they are in a more commercially valuable form).

Further advantageously, the wet oxidation may produce steam. For example, in one embodiment, wherein the heat generated by the wet oxidation is sufficient to evaporate the water in the reactor, and/or wherein steam is generated by heat supplied to the reactor, the heated water vapour and incondensable gases may exit the reactor from the top and be fed to a heat exchanger (e.g., to be heat exchanged against boiler feedwater) to generate clean steam that may be used elsewhere in the process. For example, in one the steam generated from the wet oxidation (e.g., directly or indirectly) is used to supply energy to the pretreatment (e.g., directly or indirectly). For example, in one embodiment, steam resulting from the wet oxidation is fed to any stage of the process in which heat input is required. This may include introduction of the heat to pretreatment, distillation or any other step of the process in which heat is input. Steam may be introduced to a step within the process under high or low pressure. Steam from the wet oxidation may also be fed to a heat exchanger and condensed. The condensed heat exchanger fluid can then be used to supply heat to the wet oxidation, as discussed above. In certain embodiments, energy from the wet oxidation is provided to pretreatment. In one embodiment, the amount of steam that is produced in the wet oxidation is at least the quantity of steam used in a steam heating step conducted during pretreatment. In other embodiments, the steam that is produced as a result of the wet oxidation provides a portion of the steam in a steam heating step conducted during pretreatment.

Advantageously, supplying heat from the wet oxidation can in certain embodiments allow for the elimination of a boiler that would otherwise be needed to supply such heat to pretreatment. Thus, in certain embodiments, the process is conducted without utilizing a boiler to supply heat to pretreatment. In further embodiments, the wet oxidation is the only or primary source of heat for the pretreatment. For example, greater than 50% of the heat usage in the pretreatment may be supplied by wet oxidation. In further embodiments, greater than 60%, greater than 70%, greater than 80% or greater than 90% of the heat usage in the pretreatment may be supplied by wet oxidation.

In one embodiment, the reactor is provided with one or more pressure control valves that may be used to regulate the flow of liquid, solids, and/or gases from the high pressure part of the system to the relatively low pressure part of the system. For example, in one embodiment, the pressure control valve is used to maintain the pressure within the reactor (e.g., at a predetermined or actively determined value) and/or to maintain a predetermined liquid level within the reactor. In one embodiment, the pressure control valve(s) are used to maintain the reactor temperature at the predetermined reactor temperature.

In one embodiment, the wet oxidation reactor is designed to optimize energy recovery (e.g., see U.S. Pat. No. 4,100, 730). For example, in one embodiment, the steam and/or noncondensible gases are fed to a turbo-generator wherein the exhaust gases pass into a gas expander, and are used to drive a generator (e.g., to generate electricity) and/or used to drive an air compressor (e.g., used to provide the oxidant to the wet oxidation).

In one embodiment, the wet oxidation reactor is a bubble column reactor. In other embodiments, the wet oxidation reactor is a vertical tube reactor. In one embodiment, the wet oxidation reactor is a gravity pressure vessel.

Providing Salt for Use in One or More Applications

In one embodiment, a stream comprising salt from the oxidized stream resulting from wet oxidation is provided for use in one or more applications. Such stream comprising salt may be used as a process chemical, as a salt product or for any other use that is suitable for the salts. A "salt product" as used herein encompasses any composition comprising a salt originating from the process that is used outside the process of the present invention, typically as a vendible product. Inorganic salts may be used as fertilizer. Salts of organic acids may find use in various industrial processes, as additives or as vendible products, such as road salts. When used as a process chemical, the stream may be used to adjust the pH of a process stream to a value suitable for a biocatalyst such as a microorganism and/or enzyme. When used as a salt product, such as a fertilizer, the stream comprising the salt may be used to supply nutrients to soil.

Such stream comprising inorganic and/or organic salt can be the oxidized stream itself resulting from wet oxidation, or a stream derived therefrom after additional process steps. Examples of additional processing steps are described below.

For example, insoluble components may be removed from the treated stream by any known methodology, such as a solids-liquid separation. The solids-liquid separation produces a process stream comprising insoluble solids and an aqueous stream. Some non-limiting examples of a suitable solids-liquid separation techniques for removing insoluble solids are centrifugation, filtration or sedimentation. Components that may be present in the treated stream that are removed by the solids-liquid separation include sand and/or ash.

After solids-liquid separation, the aqueous stream may be concentrated. Non-limiting examples of methods for concentration of the aqueous stream include evaporation, reverse osmosis, centrifugation, membrane separation, settling or other suitable techniques. In some embodiments of the invention, between about 10% and 90% (w/w), or between about 30% and about 90% (w/w) of the liquid is removed from the aqueous stream.

In one embodiment, concentration of the aqueous stream is carried out in an evaporator unit. The evaporation may be carried out in a single-stage evaporator or a multiple-effect system may be used. Those of skill in the art can readily choose a suitable operating temperature for the evaporator unit. In some embodiments of the invention, the operating temperature of the evaporator unit can be between about 40° C. and about 145° C. It will be understood that the temperature is measured at the operating pressure, which is typically under vacuum or at atmospheric pressure, but can be at higher pressure.

The concentration produces a concentrated stream comprising the salt. The concentrated stream may be used as a process chemical, as a fertilizer or for any other use that is suitable for the salts. The salts may optionally be removed and recovered from the concentrated stream by known techniques such as extraction, anion exchange or other suitable known recovery processes. In another embodiment, the aqueous stream is not concentrated.

A stream comprising the salt (e.g., non-concentrated stream, concentrated stream, or a solid stream) may be passed to a third party that applies the stream to land as a fertilizer or to a third party, such as an intermediary, that passes the stream to a user that applies the stream to land.

Advantageously, subjecting a salt containing stream to wet oxidation reduces the relative costs of recovering and/or recycling the sulfur containing salts. For example, oxidizing sulfite salts to provide sulfate salts reduces costs and provides the sulfur in a more commercially valuable form. Notably, this is increasingly valuable for embodiments wherein the feedstock is pretreated with sulfur dioxide, wherein there is a relatively large amount of sulfur to recover. Moreover, it is advantageous when the feedstock includes potassium, as for example, in many lignocellulosic feedstocks. For example, providing a salt product that includes potassium, which is native to the feedstock, may offset arbitrage losses on ammonia and sulfate.

An embodiment of the invention is depicted in the flow-sheet described in FIG. 1. As shown in FIG. 1, an incoming lignocellulosic feedstock slurry 2 is treated with a stream of gaseous sulfur dioxide 4 (e.g., 2% to 30% dry weight of feedstock). Upon addition of the stream of gaseous sulfur dioxide 4 to the lignocellulosic feedstock slurry 2, sulfurous acid is produced, along with sulfite and/or bisulfite and/or their salts. The pretreatment 6 is conducted at a pH of between 1.0 and 2.5 and a temperature between 160° C. and 230° C. achieved with steam from stream 33 and produces a pretreated feedstock slurry 8 comprising sugars selected from xylose, glucose, arabinose, mannose and galactose, soluble products from the reaction of lignin with sulfur dioxide and/or sulfurous acid including sulfonic acids, sulfite salts, sulfonic acid salts, and soluble native lignin, and unhydrolyzed cellulose and insoluble lignin (native and sulfonated). The pretreated feedstock slurry 8 comprising the unhydrolyzed, pretreated feedstock is cooled to 40 to 60° C. Base is added at 10 to the pretreated feedstock slurry 8 to achieve a pH between 4 and 7. Treating the lignocellulosic feedstock by the addition of acid and/or base provides at least one of a sulfite, a sulfite salt, sulfurous acid, and sulfonic acid(s). In this example, the base added to adjust the pH of the pretreated feedstock is ammonium hydroxide. The addition of ammonium hydroxide produces ammonium sulfite and/or ammonium bisulfite, the relative amount of which is dependent on pH.

The pretreated feedstock slurry 8 is then subjected to enzymatic hydrolysis 14 with cellulase enzymes. The enzymatic hydrolysis 14 with cellulase enzymes is conducted by adding cellulase enzymes at 15 at a dosage of 2 to 20 mg protein per gram of cellulose for 12 to 200 hours. The cellulose hydrolysis 14 produces a hydrolyzate stream 16 comprising glucose. The hydrolyzate stream 16 resulting from the hydrolysis 14 is fed to fermentation 18 to produce ethanol using *Saccharomyces cerevisiae* yeast under conventional conditions. The fermentation 18 produces a fermented slurry 20 comprising the ethanol and carbon dioxide 22. The fermented slurry 20 is fed to distillation 22 in which ethanol is recovered. Distillation 22 produces a concentrated ethanol stream 23, which may be further concentrated by molecular sieves or other concentration methods.

The distillation 22 also produces a product-depleted stream, referred to in this example as a still bottoms stream 24 that remains after distillation 22. The still bottoms stream 24 is then subjected to a wet oxidation 28.

The wet oxidation 28 comprises the addition of an oxygen-containing stream 30. Wet oxidation of the still bottoms stream 24 is conducted at conditions to solubilise and/or oxidize a portion of the lignin and/or to produce an oxidant-treated stream 32. The sulfur in solution after wet oxidation 28 may be in the form of sulfuric acid and/or sulfate salts. The wet oxidation 28 is conducted under elevated temperature, which in this example is at least 150° C. Energy from the wet oxidation 28, in the form of a stream of high pressure steam 33 is fed back to pretreatment 6 to supply energy for that operation. The amount of steam that is produced in the wet oxidation is most advantageously at least the quantity of steam used in a steam heating step conducted during pretreatment.

The treated stream 32 is subsequently fed to a solids-liquid separation step 34 (e.g., centrifugation, filtration or sedimentation) which produces a solids stream 36 and an aqueous stream 38. The solids stream 36 may comprise sand, which includes silica, and/or ash.

The aqueous stream 38 comprises inorganic sulfate salts (e.g., ammonium sulfate and/or potassium sulfate), that may find use as a fertilizer. The aqueous stream 38 is evaporated in evaporation 39 to produce an evaporated stream 40 comprising ammonium sulfate and/or potassium sulfate. The evaporated stream 40 is then supplied for use as a fertilizer composition comprising one or more of these salts, among other components.

Figure 2:
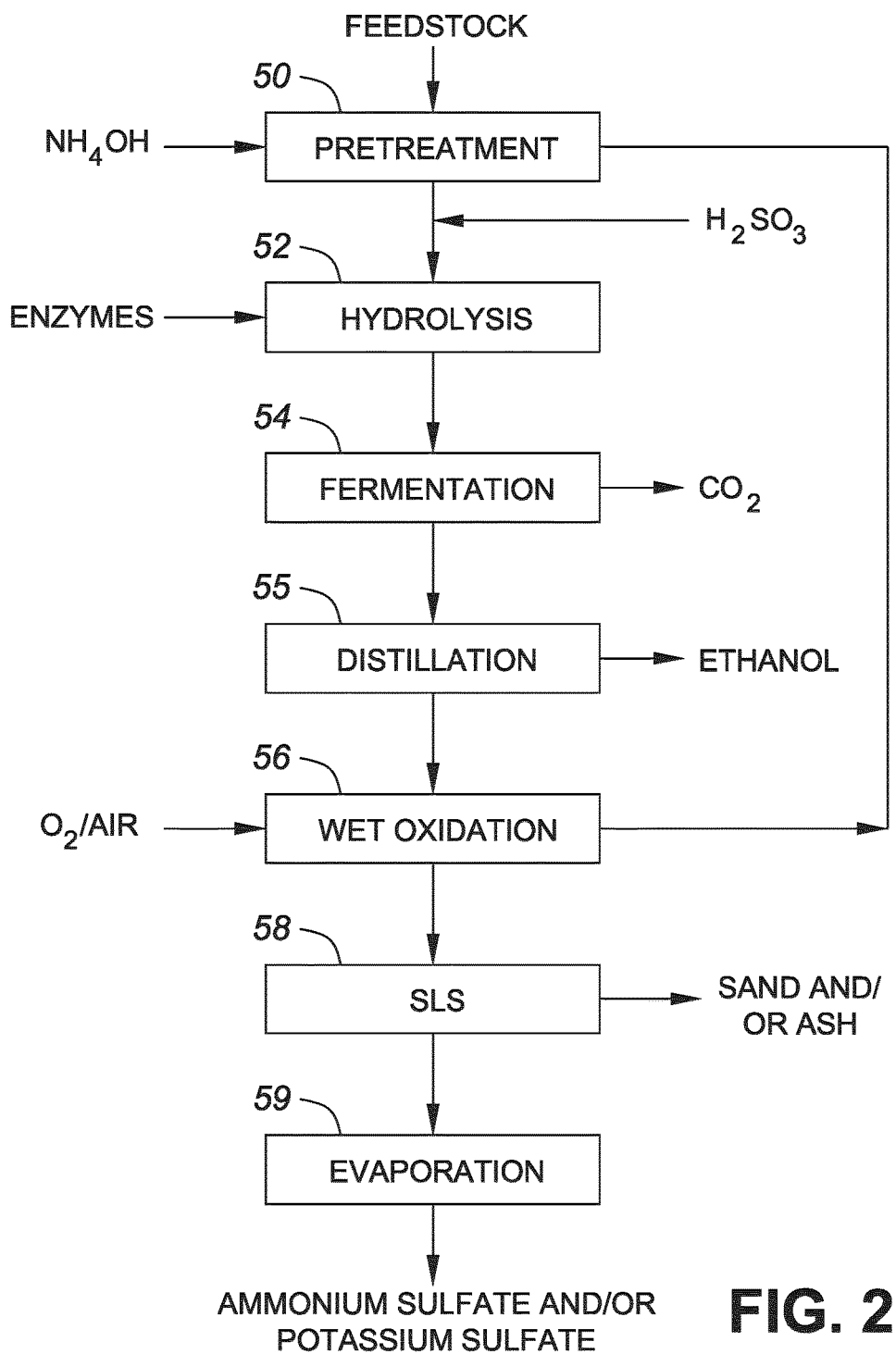
FIG. 2 shows a flow diagram showing a process conducted in accordance with one embodiment of the invention.

Referring to FIG. 2, there is shown another embodiment of the invention. A lignocellulosic feedstock (e.g., which contains potassium), which is dry or provided as a slurry, is subject to an alkali (e.g., $NH_4OH$) pretreatment 50 with heat (e.g., steam from the wet oxidation). The alkali pretreatment helps to liberate the cellulose from the lignin and make it accessible for the subsequent hydrolysis step. After a pH adjustment (e.g., addition of sulfurous acid), the pretreated slurry is subjected to an enzymatic hydrolysis 52. Upon addition of the sulfurous acid, sulfite and/or bisulfate salts may be produced (e.g., ammonium sulfite and/or potassium sulfite). The enzymatic hydrolysis 52, which may include cellulase enzymes, produces a hydrolysate stream comprising a sugar, such as glucose. The hydrolysate stream is fed to fermentation 54 to produce a fermentation product, such as an alcohol (e.g., to produce ethanol using *Saccharomyces cerevisiae* yeast). The fermentation produces a fermented stream which is distilled 55 to provide a first stream wherein the alcohol is concentrated and a second stream where the concentration of alcohol is significantly reduced (e.g., a product depleted stream). The product depleted stream, which in this embodiment may also be referred to as a still bottoms stream, is then subjected to a wet oxidation 56. The wet oxidation 56 oxidizes the sulfite salts to provide sulfate salts, and may solubilise and/or oxidize the lignin and/or unhydrolyzed cellulose. The resulting treated stream may then be subjected to a solid/liquid separation (SLS) 58, which may include centrifugation, filtration or sedimentation, to remove sand and/or ash, so that relatively pure sulfate salts can be recovered (e.g., by evaporation 59). Since the wet oxidation produces/uses a relatively large amount of energy, excess energy (e.g., in the form of a stream of high pressure steam) is optionally fed back to pretreatment. Since the amount of excess energy/steam may be similar or larger than that typically used during pretreatment, this resulting heat integration may be highly advantageous. Further advantageously, the recovered sulfate salts may be used and/or sold for use in fertilizers and/or used within the process.

Figure 3:
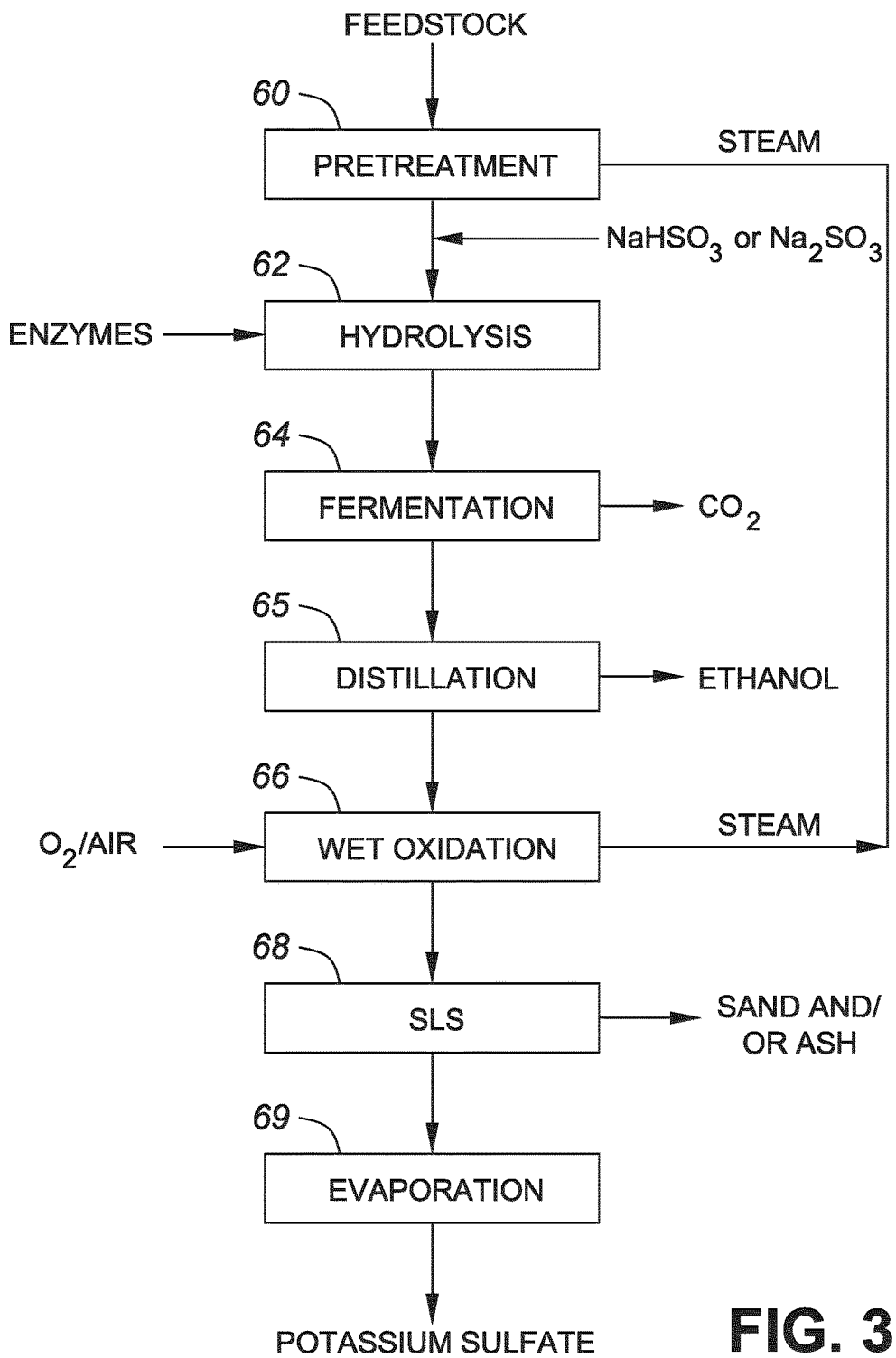
FIG. 3 shows a flow diagram showing a process conducted in accordance with one embodiment of the invention.

Referring to FIG. 3, there is shown another embodiment of the invention. A lignocellulosic feedstock (e.g., which contains potassium), which is dry or provided as a slurry, it subject to an autohydrolysis pretreatment (e.g., using steam from the wet oxidation). The autohydrolysis pretreatment 60 may help to liberate the cellulose from the lignin and/or make it accessible for the subsequent hydrolysis step. After a pH adjustment with $NaHSO_3$ or $Na_2SO_3$, the pretreated slurry is subjected to an enzymatic hydrolysis 62. Upon adjustment of the pH with $NaHSO_3$ or $Na_2SO_3$, sulfite and/or bisulfate salts may be produced or be in solution (e.g., potassium sulfite or sodium bisulfite). The enzymatic hydrolysis, which may include cellulase enzymes, produces a hydrolysate stream comprising a sugar, such as glucose. The hydrolysate stream is fed to fermentation 64 to produce a fermentation product, such as an alcohol (e.g., to produce ethanol using *Saccharomyces cerevisiae* yeast). The fermentation produces a fermented stream which is distilled 65 to provide a first stream wherein the alcohol is concentrated and a second stream where the concentration of alcohol is significantly reduced (e.g., a product depleted stream). The product depleted stream, which in this embodiment may also be referred to as a still bottoms stream, is then subjected to a wet oxidation 66. The wet oxidation oxidizes the sulfite salts to provide sulfate salts, and may also solubilise and/or oxidize the lignin and/or unhydrolyzed cellulose. The resulting treated stream may then be subjected to a solid/liquid separation (SLS) 68, which may include centrifugation, filtration or sedimentation, to remove sand and/or ash, so that relatively pure sulfate salts can be evaporated 69. Since the wet oxidation produces and/or uses a relatively large amount of energy, excess energy (e.g., in the form of a stream of high pressure steam) is optionally fed back to pretreatment. For example, the stream of high pressure steam may be generated by the above-described autohydrolysis pretreatment 60.

Since the amount of excess energy/steam may be similar or larger than that typically used during pretreatment, this resulting heat integration may be highly advantageous. Further advantageously, the recovered sulfate salts may be used and/or sold for use in fertilizers and/or used within the process.

Figure 4:
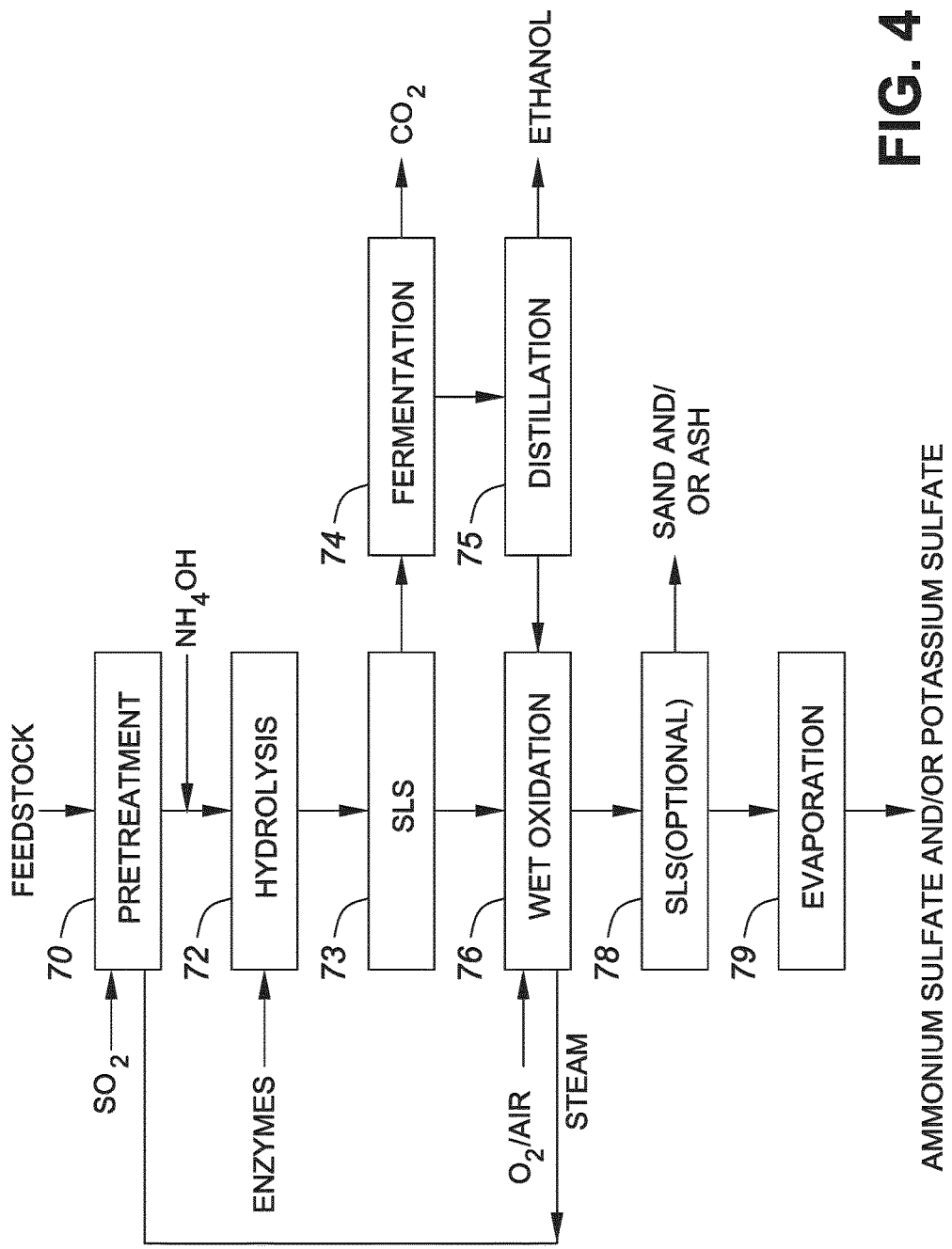
FIG. 4 shows a flow diagram showing a process conducted in accordance with one embodiment of the invention.

Referring to FIG. 4, there is shown another embodiment of the invention. A lignocellulosic feedstock (e.g., which contains potassium), which is dry or provided as a slurry, is subjected to an acid pretreatment (e.g., sulfur dioxide and/or sulfurous acid). The acid pretreatment 70 may help to liberate the cellulose from the lignin and/or make it accessible for the subsequent hydrolysis step. After a pH adjustment involving the addition of alkali (e.g., $NH_4OH$), the pretreated slurry is subjected to an enzymatic hydrolysis 72. Upon addition of the alkali (e.g., $NH_4OH$), sulfite and/or bisulfite salts may be produced (e.g., ammonium and/or potassium sulfite). The enzymatic hydrolysis, which may include cellulase enzymes, produces a hydrolysate stream comprising a sugar, such as glucose. The hydrolysate stream is then subjected to a solid/liquid separation (SLS) 73 that provides a first aqueous stream (e.g., including sugar) to fermentation 74, and a second stream including solids (e.g., including insoluble lignin) to wet oxidation 76. The fermentation produces a fermented solution/slurry (e.g., including a fermentation product such as ethanol), which is distilled 75 to provide a first stream wherein the ethanol is concentrated and a second stream where the concentration of alcohol is significantly reduced (e.g., a product depleted stream). The product depleted stream, which in this embodiment may also be referred to as a still bottoms stream, is optionally fed to the wet oxidation 76. The wet oxidation 76 oxidizes any sulfite salts fed therein to sulfate salts, and may also solubilise and/or oxidize the lignin and/or unhydrolyzed cellulose. The resulting treated stream may then be subjected to a solid/liquid separation (SLS) 78, which may include centrifugation, filtration or sedimentation, to remove sand and/or ash, so that relatively pure sulfate salts can be recovered by evaporation 79. Since the wet oxidation produces/uses a relatively large amount of energy, excess energy (e.g., in the form of a stream of high pressure steam) is optionally fed back to pretreatment. Since the amount of excess energy/steam may be similar or larger than that typically used during pretreatment, this resulting heat integration may be highly advantageous. Further advantageously, the recovered sulfate salts may be used and/or sold for use in fertilizers and/or used within the process.

Figure 5:
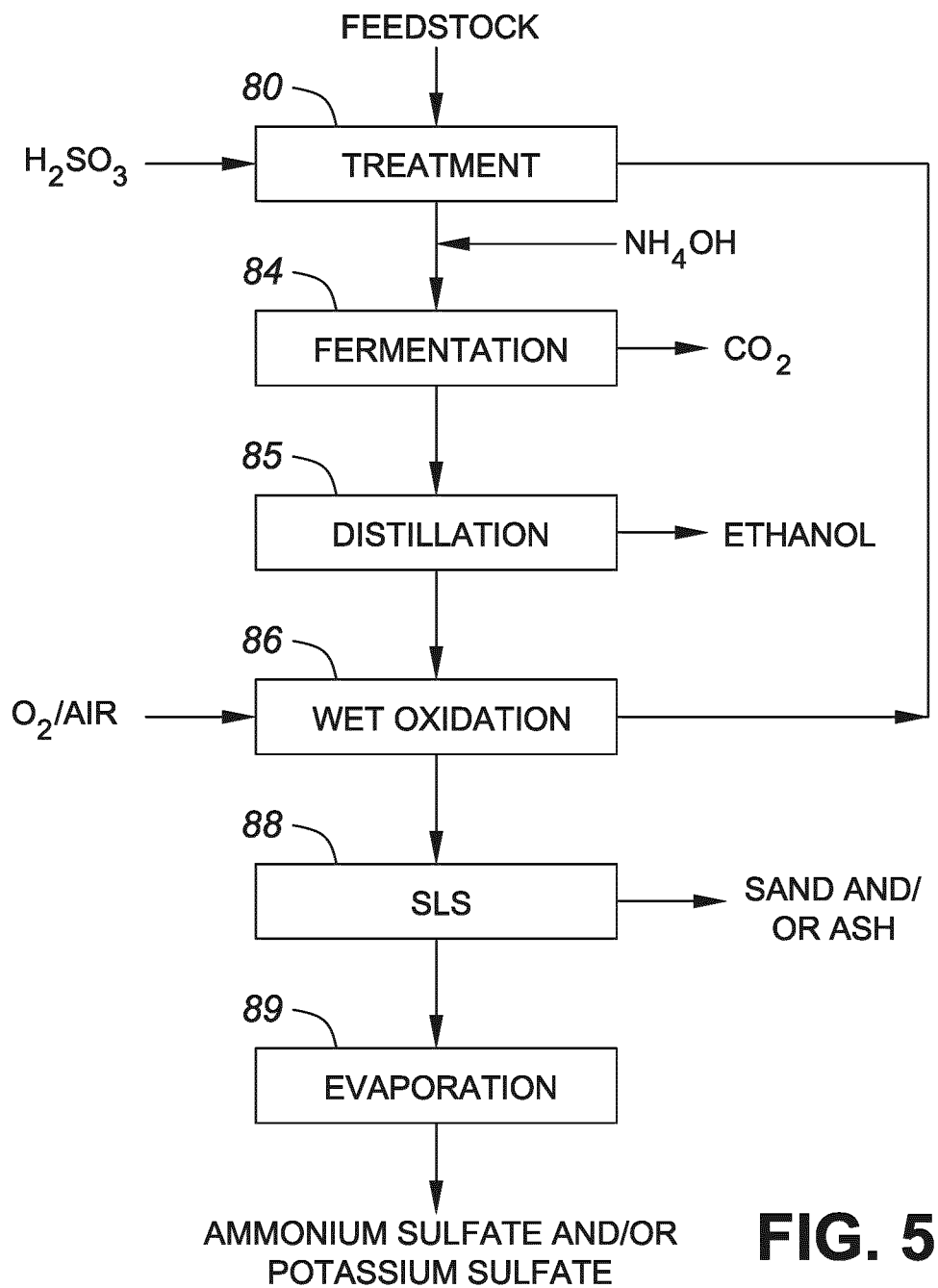
FIG. 5 shows a flow diagram showing a process conducted in accordance with one embodiment of the invention.

Referring to FIG. 5, there is shown another embodiment of the invention. A lignocellulosic feedstock (e.g., which contains potassium), which is dry or provided as a slurry, is subject to an acid treatment 80 with heat (e.g., steam from the wet oxidation, which in one embodiment is provided under relatively high pressure). The acid treatment, which includes the addition of sulfur dioxide or sulfurous acid, may help to liberate the cellulose from the lignin and/or to hydrolyze the hemicellulose and/or cellulose to a sugar (e.g., glucose). After this chemical hydrolysis, the pH of the treated slurry is adjusted with base (e.g., $NH_4OH$). Upon addition of the $NH_4OH$, sulfite and/or bisulfite salts may be produced (e.g., ammonium sulfite and/or potassium sulfite). The pH-adjusted stream is fed to fermentation 84 to produce a fermentation product, such as an alcohol (e.g., to produce ethanol using *Saccharomyces cerevisiae* yeast). The fermentation produces a fermented stream that is distilled 85 to provide a first stream wherein the alcohol is concentrated and a second stream where the concentration of alcohol is significantly reduced (e.g., a product depleted stream). The product depleted stream, which in this embodiment may also be referred to as a still bottoms stream, is then subjected to a wet oxidation 86. The wet oxidation oxidizes the sulfite salts to provide sulfate salts, and may also solubilise and/or oxidize the lignin and/or unhydrolyzed cellulose. The resulting treated stream may then be subjected to an optional solid/liquid separation (SLS) 88, which may include centrifugation, filtration or sedimentation, to remove sand and/or ash, so that relatively pure sulfate salts can be recovered by evaporation 89. Since the wet oxidation produces/uses a relatively large amount of energy, excess energy (e.g., in the form of a stream of high pressure steam) is optionally fed back to pretreatment. Since the amount of excess energy/steam may be similar or larger than that typically used during pretreatment, this resulting heat integration may be highly advantageous. Further advantageously, the recovered sulfate salts may be used and/or sold for use in fertilizers and/or used within the process.

As discussed above, these processes optionally allow for heat integration, wherein steam generated during the wet oxidation is used for pretreatment of the lignocellulosic feedstock, and/or other stages of the process in which steam may be introduced. Advantageously, heat integration may improve the process economics. More specifically, supplying heat from the wet oxidation to other stages of the process in which steam is input may allow for process simplification, as the process energy for such stages need not be provided by a separate boiler, such as one fueled by the combustion of lignin. In this regard, since lignin does not need to be separated from a process stream, further process simplification can be realized in that the specialized equipment for the separation, such as a filter press, may no longer be needed. Further, drawbacks associated with lignin separation may be avoided, including sugar loss and energy to evaporate the stream, thereby potentially improving the yield of fermentation product.

Wet oxidation may also offer other potential advantages in certain stages of the process. For example, in certain embodiments, wet oxidation may simplify handling of a product-depleted stream resulting from concentration of the fermentation product, such as by distillation. In particular, treating the still bottoms via wet oxidation may provide various advantages relative to treating the still bottoms via anaerobic digestion.

Anaerobic digestion, which is a collection of processes in which microorganisms break down organic components in the absence of oxygen, is often used to treat and/or remove organic compounds in order to manage waste products. For example, the organic waste may be fed to one or more anaerobic digestion reactors or tanks, wherein anaerobic bacteria digest the waste and produce gases such as methane, carbon dioxide, and hydrogen sulfide (e.g., biogas). In cellulosic ethanol plants, the biogas from the anaerobic digestion may be used to generate heat used within the process and/or to generated electricity, thus reducing the carbon footprint.

However, as described above, salts are often produced upon the addition of acid or base to the incoming feedstock or during the process. Waste treatment systems such as anaerobic digestion may require removal of sulfite and/or sulfate salts for optimal performance due to their inhibitory effect on the microbes. However, wet oxidation does not necessarily require removal of such salts, thus potentially eliminating the need for a step of the process that otherwise might be required. Although, the processes described herein do not require anaerobic digestion, in one embodiment, both anaerobic digestion and wet oxidation stages are included in the same process.

Yet a further advantage realized in certain embodiments is that using salt resulting from the wet oxidation, such as inorganic salt as fertilizer can aid in off-setting the cost of the process chemical, such as acid or base used for pH adjustment to produce sugar and/or to prepare the feedstock for enzymatic hydrolysis. As discussed above, salt produced in the process may contain sulfur-containing salts, which have particular value in land application and thus can be a source of revenue for a plant. Examples of such salts include ammonium sulfate and potassium sulfate. The production of a fertilizer comprising potassium sulfate is particularly advantageous in that the potassium is native to the feedstock and so utilizes a component in the incoming feedstock that otherwise would likely have no or limited use. The salt obtained from the process may find other uses. In further embodiments, the salt can be used as a process chemical. For example, the salt can be added to a stream that contains acid or base to adjust its pH, thereby reducing chemical consumption.

The present invention has been described with regard to one or more embodiments. However, it will be apparent to persons skilled in the art that a number of variations and modifications can be made without departing from the scope of the invention as defined in the claims.

The invention claimed is:

1. A process for producing one or more products from a lignocellulosic feedstock comprising:
   (i) treating the lignocellulosic feedstock to produce sugar in one or more stages comprising addition of acid, base, or a combination thereof, wherein the addition of acid, base or a combination thereof provides at least one of a sulfite, a sulfite salt, sulfurous acid, and a sulfonic acid,
      wherein step (i) optionally comprises addition of cellulase enzymes to produce glucose;
   (ii) fermenting sugar produced in one or more of the stages of step (i) to produce a fermentation product;
   (iii) recovering the fermentation product, thereby producing a stream of concentrated fermentation product;
   (iv) treating an upstream process stream by wet oxidation to produce a treated stream comprising a salt, the process stream originating from the process and comprising:
      (a) lignin,
      (b) a lignosulfate, or
      (c) a combination thereof; and
   (v) providing a stream comprising salt from the treated stream of step (iv) for use as a salt product, as a process chemical for introduction within the process, or a combination thereof.

2. A process for producing one or more products from a lignocellulosic feedstock comprising:

(i) treating the lignocellulosic feedstock by contacting same with an acid or base with addition of heat to produce a pretreated feedstock;
(ii) adjusting the pH of the pretreated feedstock with an acid or base to produce a pretreated feedstock having a pH at which cellulase enzymes can hydrolyze cellulose to glucose, wherein the addition of acid or base provides at least one of a sulfite, a sulfite salt, sulfurous acid, and a sulfonic acid;
(iii) hydrolyzing the pretreated feedstock with cellulase enzymes to produce glucose;
(iv) fermenting at least the glucose to produce a fermentation product;
(v) recovering the fermentation product, thereby producing a stream of concentrated fermentation product;
(vi) treating an upstream process stream, which originates from the process and comprises the at least one of a lignin, a lignosulfate, and a combination thereof, by wet oxidation to produce a treated stream comprising a salt; and
(vii) providing a stream comprising salt from the treated stream of step (vi) for use as a salt product, as a process chemical for introduction within the process, or a combination thereof.

3. A process for producing one or more products from a lignocellulosic feedstock comprising:
(i) treating the lignocellulosic feedstock by contacting same with at least heat to produce a pretreated feedstock, the treatment including adding an acid;
(ii) optionally adjusting the pH of the pretreated feedstock with a base to produce a pretreated feedstock having a pH at which cellulase enzymes can hydrolyze cellulose to glucose, wherein the addition of the acid, base, or combination thereof provides at least one of a sulfite, a sulfite salt, sulfurous acid, and a sulfonic acid;
(iii) hydrolyzing the pretreated feedstock with cellulase enzymes to produce glucose;
(iv) fermenting at least the glucose to produce a fermentation product;
(v) recovering the fermentation product, thereby producing a stream of concentrated fermentation product;
(vi) treating an upstream process stream, which originates from the process and comprises lignin, a lignosulfate, or a combination thereof by wet oxidation, to produce a treated stream comprising a salt;
(vii) introducing steam energy from step (vi) to the step of pretreating; and
(viii) providing a stream comprising salt from the treated stream of step (vi) for use as a salt product, as a process chemical for introduction within the process, or a combination thereof.

4. The process of claim 1 wherein a product-depleted stream is produced upon recovering the fermentation product, and wherein the upstream process stream comprises the product-depleted stream.

5. The process of claim 1, wherein the treated stream comprising the salt is concentrated prior to the step of providing.

6. The process of claim 5, wherein the treated stream comprising the salt is concentrated by evaporation, reverse osmosis, or a combination thereof, prior to the step of providing.

7. The process of claim 5, wherein the treated stream comprising the salt is subjected to a solids-liquid-separation prior to the step of concentrating.

8. The process of claim 1, wherein the treating of the lignocellulosic feedstock comprises the addition of sulfurous acid, sulfur dioxide, or a combination thereof.

9. The process claim 1, wherein the salt product is a fertilizer and the step of providing comprises directly or indirectly passing the fertilizer to a user that applies the fertilizer to land.

10. The process of claim 1, wherein the wet oxidation comprises the addition of air or oxygen.

11. The process of claim 1, wherein the salt is ammonium sulfate, potassium sulfate, or a combination thereof.

12. The process of claim 1, wherein step (i) of treating comprises introduction of steam to achieve a temperature of at least 160° C.

13. The process of claim 1, wherein the step (i) of treating is conducted with the addition of an amount of steam, and wherein the wet oxidation produces an amount of steam that is at least the amount of steam for pretreating.

14. The process of claim 1, wherein the wet oxidation is conducted at a temperature of at least 160° C.

15. The process of claim 1, wherein the stream of concentrated fermentation product is produced by distillation.

16. The process of claim 1, wherein during the process at least 90% of the heat provided to the step (i) of treating is from the wet oxidation.

17. The process of claim 1, comprising introducing steam energy from step (iv) to a step of the process in which heat is input.

18. The process of claim 17, wherein the steam energy from step (iv) is introduced into step (i) of treating.

19. The process of claim 18, wherein the acid comprises sulfur dioxide, sulfurous acid, or a combination thereof.

20. The process of claim 19, wherein the salt comprises a sulfate salt.

21. The process of claim 1, wherein the acid comprises sulfur dioxide, sulfurous acid, or a combination thereof.

22. The process of claim 1, wherein the salt comprises a sulfate salt.

23. The process of claim 1, wherein the process stream comprises (a) lignin, and wherein the lignin comprises native or sulfonated solid lignin.

24. The process of claim 1, wherein the process stream comprises (a) lignin, and wherein the lignin comprises dissolved lignin.

* * * * *

UNITED STATES PATENT AND TRADEMARK OFFICE
CERTIFICATE OF CORRECTION

PATENT NO. : 10,421,667 B2
APPLICATION NO. : 15/550584
DATED : September 24, 2019
INVENTOR(S) : Patrick J. Foody et al.

It is certified that error appears in the above-identified patent and that said Letters Patent is hereby corrected as shown below:

On the Title Page

On Page 2, Column 2, Item (56), Line 74, under Other Publications, delete "Bioresouces" and insert --Bioresources--.

On Page 3, Column 1, Item (56), Line 27, under Other Publications, delete "Comparitive" and insert --Comparative--.

On Page 3, Column 1, Item (56), Line 34, under Other Publications, delete "Biotehncol." and insert --Biotechnol.--.

On Page 3, Column 1, Item (56), Line 45, under Other Publications, delete "H25O4" and insert --H2SO4--.

On Page 3, Column 2, Item (56), Line 30, under Other Publications, delete "Comparitive" and insert --Comparative--.

On Page 4, Column 1, Item (56), Line 4, under Other Publications, delete "Lianocellulosic" and insert --Lignocellulosic--.

In the Specification

In Column 10, Line 37, delete "Myceliopthora" and insert --Myceliophthora--.

In Column 19, Line 16, delete "bisulfate" and insert --bisulfite--.

Signed and Sealed this
Sixteenth Day of February, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,421,667 B2

In the Claims

In Column 23, Line 52, Claim 4, delete "claim 1" and insert --claim 1,--.

In Column 24, Line 14, Claim 9, delete "process claim" and insert --process of claim--.